(12) United States Patent
Kopelman et al.

(10) Patent No.: US 12,178,683 B2
(45) Date of Patent: *Dec. 31, 2024

(54) IMAGE REGISTRATION OF INTRAORAL IMAGES USING INK MARKINGS

(71) Applicant: Align Technology, Inc., San Jose, CA (US)

(72) Inventors: Avi Kopelman, Palo Alto, CA (US); Adi Levin, Nes Tziona (IL); Ran Katz, Hod Hasharon (IL); Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/369,750

(22) Filed: Sep. 18, 2023

(65) Prior Publication Data

US 2024/0016586 A1    Jan. 18, 2024

Related U.S. Application Data

(63) Continuation of application No. 17/023,276, filed on Sep. 16, 2020, now Pat. No. 11,793,610, which is a continuation of application No. 16/133,551, filed on Sep. 17, 2018, now Pat. No. 10,806,549, which is a
(Continued)

(51) Int. Cl.
*A61C 9/00* (2006.01)
*A61B 90/00* (2016.01)
*G06T 7/593* (2017.01)

(52) U.S. Cl.
CPC ............ *A61C 9/0053* (2013.01); *A61B 90/39* (2016.02); *G06T 7/593* (2017.01); *A61B 2090/3937* (2016.02); *A61B 2090/3991* (2016.02); *G06T 2207/10012* (2013.01); *G06T 2207/30036* (2013.01)

(58) Field of Classification Search
CPC . A61B 19/54; A61B 90/39; A61B 2090/3937; A61B 2090/3991; A61C 9/0053; G06T 2207/10012; G06T 2207/30036
USPC ............................................ 433/25; 382/128
See application file for complete search history.

(56) References Cited

U.S. PATENT DOCUMENTS 5,886,775 A * 3/1999 Houser .................... G01S 17/86
                                                                356/402
6,099,314 A    8/2000 Kopelman et al.
6,334,772 B1   1/2002 Taub et al.
(Continued)

*Primary Examiner* — Matthew M Nelson
(74) *Attorney, Agent, or Firm* — Lowenstein Sandler LLP

(57) ABSTRACT

Embodiments include receiving intraoral scan data comprising a plurality of intraoral images of a dental site generated during scanning of the dental site by an intraoral scanner, a plurality of ink markings each comprising a pattern of ink having been temporarily stamped or tattooed onto a gingival surface at the dental site prior to the scanning of the dental site, wherein at least two intraoral images of the plurality of intraoral images comprise representations of one or more ink markings of the plurality of ink markings. Embodiments further include performing registration between the plurality of intraoral images based at least in part on the one or more ink markings, generating a three-dimensional (3D) model of the dental site using the plurality of intraoral images that have undergone registration, and outputting the generated 3D model to a display.

20 Claims, 14 Drawing Sheets

Related U.S. Application Data continuation of application No. 14/165,504, filed on Jan. 27, 2014, now Pat. No. 10,111,714.

(56) References Cited

U.S. PATENT DOCUMENTS

| | | | |
|---|---|---|---|
| 6,334,853 B1 | 1/2002 | Kopelman et al. | |
| 6,463,344 B1 | 10/2002 | Pavlovskaia et al. | |
| 6,633,789 B1 | 10/2003 | Nikolskiy et al. | |
| 6,664,986 B1 | 12/2003 | Kopelman et al. | |
| 6,697,164 B1 | 2/2004 | Babayoff et al. | |
| 6,845,175 B2 | 1/2005 | Kopelman et al. | |
| 6,979,196 B2 | 12/2005 | Nikolskiy et al. | |
| 7,030,383 B2 | 4/2006 | Babayoff et al. | |
| 7,202,466 B2 | 4/2007 | Babayoff et al. | |
| 7,255,558 B2 | 8/2007 | Babayoff et al. | |
| 7,286,954 B2 * | 10/2007 | Kopelman | G16Z 99/00 700/118 |
| 7,319,529 B2 | 1/2008 | Babayoff | |
| 7,362,890 B2 * | 4/2008 | Scharlack | A61C 9/0053 382/128 |
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,894,878 B2 * | 2/2011 | Noujeim | G03B 42/042 600/407 |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,699,670 B2 * | 4/2014 | Graumann | A61B 6/032 378/162 |
| 8,908,918 B2 * | 12/2014 | Daon | A61B 34/20 128/923 |
| 8,948,482 B2 | 2/2015 | Levin | |
| D742,518 S | 11/2015 | Barak et al. | |
| 9,192,305 B2 | 11/2015 | Levin | |
| 9,202,387 B2 * | 12/2015 | Gilboa | G09B 23/28 |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,123,706 B2 | 11/2018 | Elbaz et al. | |
| 10,136,972 B2 | 11/2018 | Sabina et al. | |
| 10,380,212 B2 | 8/2019 | Elbaz et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,507,087 B2 | 12/2019 | Elbaz et al. | |
| 10,517,482 B2 | 12/2019 | Sato et al. | |
| 10,695,150 B2 | 6/2020 | Kopelman et al. | |
| 10,708,574 B2 | 7/2020 | Furst et al. | |
| 10,772,506 B2 | 9/2020 | Atiya et al. | |
| 10,813,727 B2 | 10/2020 | Sabina et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| 11,013,581 B2 | 5/2021 | Sabina et al. | |
| D925,739 S | 7/2021 | Shalev et al. | |
| 11,096,765 B2 | 8/2021 | Atiya et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 11,744,681 B2 | 9/2023 | Avi et al. | |
| 11,759,277 B2 | 9/2023 | Shalev et al. | |
| 2003/0065259 A1 * | 4/2003 | Gateno | A61C 7/08 600/407 |
| 2004/0002642 A1 * | 1/2004 | Dekel | G06T 7/74 600/407 |
| 2004/0071367 A1 * | 4/2004 | Irani | G06T 7/38 382/284 |
| 2004/0138556 A1 * | 7/2004 | Cosman | A61B 90/10 600/473 |
| 2006/0164682 A1 * | 7/2006 | Lev | H04N 1/387 358/1.15 |
| 2006/0251220 A1 * | 11/2006 | Young | A61C 1/084 378/204 |
| 2007/0163139 A1 * | 7/2007 | Russell | A61B 90/39 33/758 |
| 2008/0009718 A1 * | 1/2008 | Zohman | A61B 90/39 600/426 |
| 2009/0054910 A1 * | 2/2009 | Zheng | A61B 17/1725 382/128 |
| 2009/0177077 A1 * | 7/2009 | Piferi | G01R 33/3415 600/414 |
| 2009/0291407 A1 * | 11/2009 | Kuo | A61B 6/512 433/24 |
| 2010/0290693 A1 * | 11/2010 | Cohen | A61B 5/0044 382/134 |
| 2011/0038516 A1 * | 2/2011 | Koehler | G06T 7/149 382/128 |
| 2011/0050848 A1 * | 3/2011 | Rohaly | G06T 15/10 348/43 |
| 2012/0076417 A1 * | 3/2012 | Yoshii | G06V 10/50 382/190 |
| 2012/0215096 A1 * | 8/2012 | Gilboa | A61B 34/20 600/426 |
| 2012/0238864 A1 * | 9/2012 | Piferi | G01R 33/285 600/414 |
| 2012/0281808 A1 * | 11/2012 | Graumann | A61B 6/584 378/41 |
| 2012/0302863 A1 * | 11/2012 | O'Neill | A61B 90/39 600/407 |
| 2013/0004085 A1 * | 1/2013 | Bai | G06T 3/14 382/209 |
| 2013/0135429 A1 * | 5/2013 | Lablans | H04N 23/635 348/36 |
| 2013/0273492 A1 * | 10/2013 | Suttin, Sr. | A61C 8/0001 433/29 |
| 2014/0056495 A1 * | 2/2014 | Janssens | G06T 5/80 378/207 |
| 2014/0098100 A1 * | 4/2014 | Dane | H04N 13/302 345/427 |
| 2014/0105474 A1 * | 4/2014 | Lee | G06T 7/0012 382/128 |
| 2014/0105490 A1 * | 4/2014 | Kokemohr | G06T 5/92 382/167 |
| 2014/0126767 A1 * | 5/2014 | Daon | A61B 90/39 382/103 |
| 2014/0172375 A1 * | 6/2014 | Grove | A61C 7/002 703/1 |
| 2014/0270067 A1 * | 9/2014 | Clark | A61B 50/30 378/163 |

(56) References Cited

U.S. PATENT DOCUMENTS

| | | |
|---|---|---|
| 2015/0097827 A1* | 4/2015 | Cohen .................... G06T 5/77 |
| | | 345/420 |
| 2015/0209118 A1* | 7/2015 | Kopelman ........... A61C 9/0053 |
| | | 433/214 |
| 2015/0223906 A1* | 8/2015 | O'Neill ................ A61B 6/0492 |
| | | 600/407 |
| 2019/0388193 A1 | 12/2019 | Saphier et al. |
| 2020/0197136 A1* | 6/2020 | Belcari .................... G06T 7/33 |
| 2021/0059796 A1 | 3/2021 | Weiss et al. |
| 2021/0121049 A1 | 4/2021 | Rudnitsky et al. |
| 2021/0128281 A1 | 5/2021 | Peleg |
| 2021/0137653 A1 | 5/2021 | Saphier et al. |
| 2021/0196152 A1 | 7/2021 | Saphier et al. |

* cited by examiner

IMAGE REGISTRATION OF INTRAORAL IMAGES USING INK MARKINGS

RELATED APPLICATIONS

The present application is a continuation of U.S. patent application Ser. No. 17/023,276, filed Sep. 16, 2020, which is a continuation of U.S. patent application Ser. No. 16/133,551, filed Sep. 17, 2018, which is a continuation of U.S. patent application Ser. No. 14/165,504, filed Jan. 27, 2014, each of which are incorporated by reference herein.

TECHNICAL FIELD

Embodiments of the present invention relate to the field of intraoral scanning and, in particular, to a system and method for improving the results of intraoral scanning in oral cavities that lack one or more teeth.

BACKGROUND

In prosthodontic procedures designed to implant a dental prosthesis in the oral cavity, the dental site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and to prevent infection of the gums via the interface between the prosthesis and the dental site, for example.

Some procedures also call for removable prosthetics to be fabricated to replace one or more missing teeth, such as a partial or full denture, in which case the surface contours of the areas where the teeth are missing need to be reproduced accurately so that the resulting prosthetic fits over the edentulous region with even pressure on the soft tissues.

In some practices, the dental site is prepared by a dental practitioner, and a positive physical model of the dental site is constructed using known methods. Alternatively, the dental site may be scanned to provide 3D data of the dental site. In either case, the virtual or real model of the dental site is sent to the dental lab, which manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry has to be altered to avoid the collision, which may result in the coping design being less optimal. Further, if the area of the preparation containing a finish line lacks definition, it may not be possible to property determine the finish line and thus the lower edge of the coping may not be property designed. Indeed, in some circumstances, the model is rejected and the dental practitioner then re-scans the dental site, or reworks the preparation, so that a suitable prosthesis may be produced.

In orthodontic procedures it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a three-dimensional (3D) model of a dental site in the oral cavity is an initial procedure that is performed. When the 3D model is a virtual model, the more complete and accurate the scans of the dental site are, the higher the quality of the virtual model, and thus the greater the ability to design an optimal prosthesis or orthodontic treatment appliance(s).

Scanning of the dental site is complicated by regions in which a patient is missing teeth, referred to as edentulous regions. For example, in cases where two or more adjacent teeth are missing, there may be a large span of soft tissue that needs to be scanned. Such regions can be difficult to scan.

Some intraoral scanners are used in conjunction with a powder that is applied to a dental region. The powder may include particles that reflect light, with the goal of providing measurable points in the dental site. For such systems, these particles may be used to aid image registration when they operate as intended. However, the powder often does not connect well to soft tissue, and in particular to wet soft tissue. Additionally, the powder may become wet and/or wash away during scanning, decreasing an accuracy of later image registration. Additionally, many patients do not like having the powder applied to their teeth and in their mouth. Having to powder the teeth can have drawbacks such as:
1. All areas have to be powdered and the thickness of the powder layer is not homogeneous, which compromises accuracy (e.g., since the surface is not scanned directly);
2. If the scanner head touches the powder, it sticks to the optics and introduces noise to the scan;
3. The powder can be costly;
4. Some people are allergic to the powder; and
5. Color scanning of the teeth is not possible as it is all painted in white.

BRIEF DESCRIPTION OF THE DRAWINGS

The present invention is illustrated byway of example, and not byway of limitation, in the figures of the accompanying drawings.

DETAILED DESCRIPTION

Figure 1:
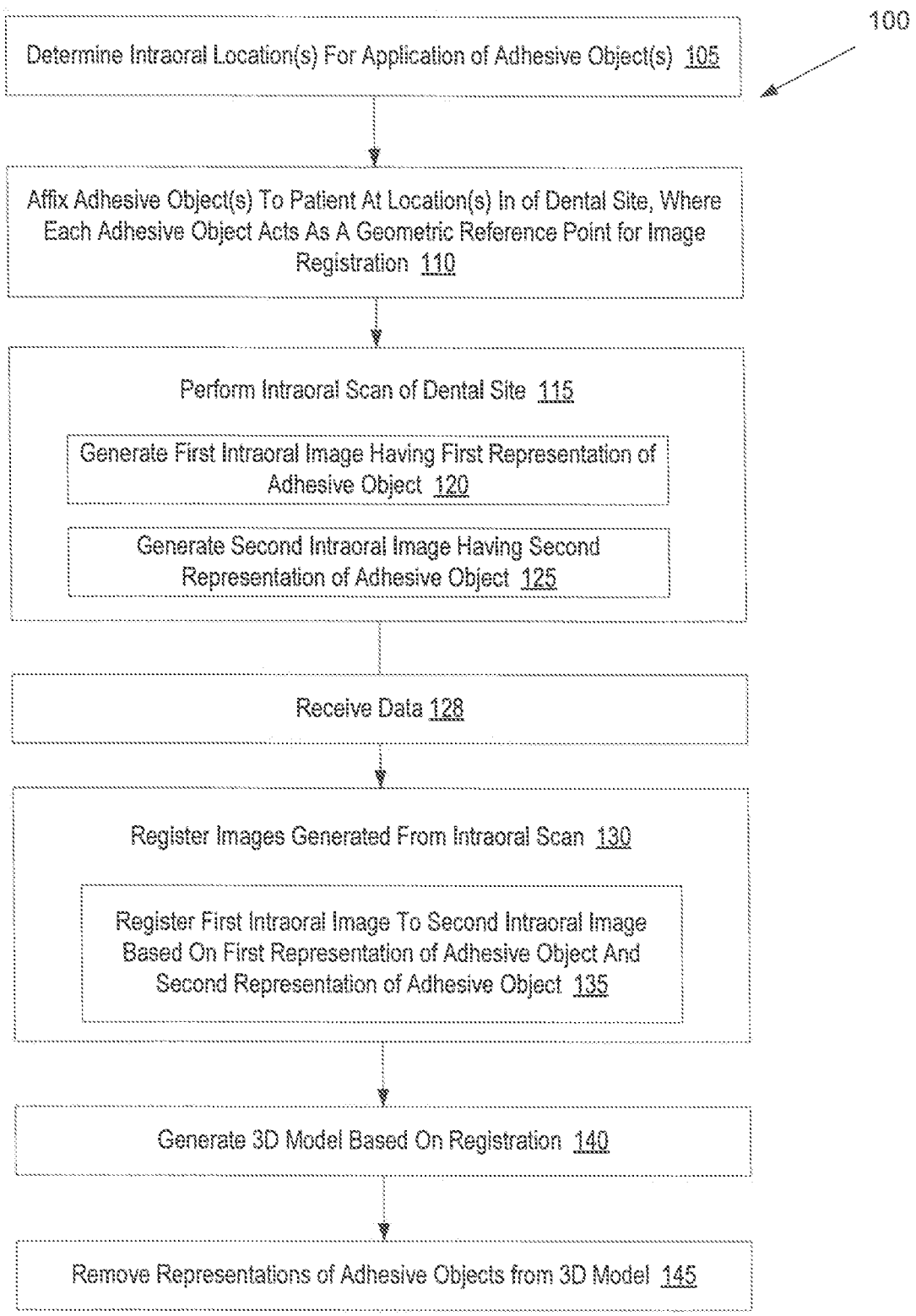
FIG. 1 illustrates a flow diagram for a method of performing intraoral scanning, in accordance with embodiments of the present invention.

Described herein is a method and apparatus for improving the quality of intraoral scans taken of dental sites for patients missing some or all of their teeth. One or more adhesive objects may be placed at dental sites in a patients oral cavity where teeth are missing. The adhesive objects may have a body with a particular shape, may have an adhesive on a lower surface of the body, and may have a feature on an upper surface of the body. The shape of the body and/or the feature on the upper surface (e.g., including a pattern and/or one or more colors) provides a geometrical or optical reference point for image registration of images generated by an intraoral scanner. In one embodiment, the body of the adhesive object is composed of a different material than the adhesive. In one embodiment, the adhesive object has a structure, shape, or pattern that does not substantially change during intraoral scanning (e.g., that does not wash away, such as may occur with powders). The adhesive object may also be an ink that is stamped onto the dental sites (e.g., onto a gingival surface) with a particular shape or pattern. The stamped ink may provide a reference point for image registration.

In one embodiment, a processing device receives intraoral images from an intraoral scan of a patient. The intraoral images may be discrete images (e.g., point-and-shoot images) or frames from an intraoral video (e.g., a continuous scan). Some of the intraoral images may include representations of an adhesive object (or multiple adhesive objects) affixed to a dental site (e.g., attached to the gingival tissue in a dental arch) at a target area. The adhesive object may have known properties and provides a reference point for image registration. The processing device performs image registration of the intraoral images. This may include performing image registration (i.e., image "stitching") between at least two intraoral images (scans) that each include a representation of at least a portion of the adhesive object. If the properties of the adhesive object are known, this information may facilitate (e.g., increase an accuracy and/or speed of) the image registration. By having a known dimension, the portion of the image which includes the adhesive object, or parts thereof, can be subtracted out from the scanned object, thereby leaving behind the original object's shape without the presence of the reference adhesive object. Additionally, if the shape, size, pattern, color, etc. of the adhesive object are known, then even if only a portion of the adhesive object is captured in an intraoral image, a shape, pattern, size, color, etc. of the remainder of the adhesive object may be extrapolated based on the known properties of that adhesive object.

The adhesive object may also be a 3-dimensional (3D) object that is itself scanned as part of the process, such that the portions of the object which are scanned in multiple images may be used as a common reference object when trying to stitch the individual images together and create a singular image to be used for dental prosthesis or orthodontic appliance fabrication. The 3D object geometry can be subtracted from the 3D generated model.

FIG. 1 illustrates a flow diagram for a method 100 of performing intraoral scanning, in accordance with embodiments of the present invention. Some aspects of the method 100 may be performed by an operator of an intraoral scanner (e.g., a dental practitioner), while other aspects of method 100 are performed by processing logic that comprises hardware (e.g., circuitry, dedicated logic, programmable logic, microcode, etc.), software (such as instructions run on a processing device), or a combination thereof. In one embodiment, processing logic is computing device 305 of FIG. 3.

At block 105 of method 100, one or more intraoral locations (e.g., of a dental site) are determined to be candidates for application of adhesive objects. The one or more intraoral locations may be manually determined by a dental practitioner, or may be determined by processing logic based on information provided by the dental practitioner (e.g., based on an indication of which of a patient's teeth are missing). In one embodiment, the dental practitioner uses a graphical user interface or other interface to indicate the patient's missing teeth. Processing logic may then identify a target area of the dental site that contains primarily or only soft tissue (e.g., edentulous regions). Such an edentulous region may prevent or complicate a successful intraoral scan of the patient because the soft tissue may lack distinctive features (e.g., geometrical features) having a definition that is suitable for performing image registration (i.e. the tissue contours may be too smooth to allow individual snapshots to be accurately registered to each other). For example, soft tissue may not permit a surface shape measurement that is usable for accurate image registration. The identified target area may be part of a dental site that forms the focus of a particular dental procedure for the patient. It may be desirable to perform an intraoral scan of the target area to obtain 3D topographical or surface data thereof (e.g., to form a 3D virtual model of the target area). The target area is typically part of a dental site on which a particular procedure is to be performed, and in some cases may include full mandibular or maxillary arches, or both arches such as would be the case of full denture treatment and fully-edentulous implant treatments (including implant-supported dentures).

The manner in which the oral cavity is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes the edentulous region, the neighboring abutment teeth and the opposing arch and dentition. Thus, the dental practitioner may also input the identity of a procedure to be performed. For this purpose, the dental practitioner may choose the procedure from a number of preset options on a drop-down menu or the like, from icons or via any other suitable graphical input interface. Alternatively, the identity of the procedure may be input in any other suitable way, for example by means of preset code, notation or any other suitable manner, processing logic having been suitably programmed to recognize the choice made by the user. By way of non-limiting example, dental procedures may be broadly divided into prosthodontic (restorative) and orthodontic procedures, and then further subdivided into specific forms of these procedures. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances.

A type of scanner to be used may also be input, typically by a dental practitioner choosing one among a plurality of options. If the scanner that is being used is not recognizable by processing logic, it may nevertheless be possible to input operating parameters of the scanner thereto instead. For example, the optimal spacing between a head of the scanner and scanned surface can be provided, as well as the capture area (and shape thereof) of the dental surface capable of being scanned at this distance. Alternatively, other suitable scanning parameters may be provided.

Processing logic may identify spatial relationships that are suitable for scanning the dental site so that complete and accurate image data may be obtained for the procedure in question. Processing logic may establish an optimal manner for scanning a target area of the dental site. Further, processing logic may compute an optimal placement for the adhesive object (or objects) based on the missing teeth or on other information. Processing logic may then identify to a dental practitioner one or more locations (e.g., the optimal placement) at which an adhesive object is recommended based on the indication by the dental practitioner of the patient's missing teeth or based on other information. Processing logic then may identify to the dental practitioner particular locations to place adhesive objects and/or a placement pattern for multiple adhesive objects. Processing logic may take into consideration a field of view of an intraoral scanner to be used when recommending placement locations for the adhesive objects to ensure that image registration will be successful.

Having identified the target area and/or locations for placement of adhesive objects, a scanning protocol is identified or determined by relating the type of scanner, resolution thereof, capture area at an optimal spacing between the scanner head and the dental surface to the target area, etc.

For a point-and-shoot scanning mode, the scanning protocol comprises a series of scanning stations spatially associated with the dental surfaces of the target area. Preferably, overlapping of the images or scans capable of being obtained at adjacent scanning stations is designed into the scanning protocol to enable accurate image registration, so that intraoral images can be stitched together to provide a composite 3D virtual model. For a continuous scanning mode (video scan), scanning stations may not be identified. Instead, a practitioner may activate the scanner and proceed to move the scanner within the oral cavity to capture a video of the target area from multiple different viewpoints.

At block 110, the dental practitioner affixes one or more adhesive objects to the patient at the identified locations of the dental site (e.g., to the portions of a target area that are missing teeth). This may include stamping an ink onto the identified regions, forming extrusions onto the identified regions, placing stickers onto the identifier regions, or placing other adhesive objects onto the identified regions. Each adhesive object will act as a geometric reference point for image registration. The adhesive objects are discussed in greater detail below.

Some embodiments are described herein with reference to placing adhesive objects to dental sites that are missing one or more teeth. However, it should be noted that adhesive objects described herein may also be used in areas with teeth to improve the accuracy of the scan, increase scanning speed and/or eliminate incorrect registration. In these cases, the intraoral objects can be adhered to the soft tissue on either or both sides of the teeth or on the teeth themselves. Accordingly, it should be understood that embodiments described herein with regards to the placement and use of adhesive objects may equally apply to edentulous regions, other dental sites that are missing one or more teeth, and dental sites that include teeth.

At block 115, the dental practitioner performs an intraoral scan of the dental site including the target area and the one or more adhesive objects. This may include performing an intraoral scan of a partial or full mandibular or maxillary arch, or a partial or full scan of both arches. Performing the intraoral scan in particular may include generating a first intraoral image having a first representation of at least one portion of an adhesive object (block 120) and generating a second intraoral image having a second representation of at least a portion of the adhesive object (block 125). The first and second intraoral images may be discrete images (e.g., taken from a point-and-shoot mode) or frames of an intraoral video (e.g., taken in a continuous scanning or video mode). In one embodiment, the second representation is of the same portion of the object that is shown in the first representation. Alternatively, the second representation may be of a different portion of the object than is shown in the first representation. In the second instance, these images may be stitched if processing logic has access to information identifying the shape, pattern and/or size of the adhesive object. Each intraoral image may be a three dimensional (3D) image having a particular height, width and depth. In some embodiments, an intraoral scanner is used that generates 3D images having a depth of 12-14 mm, a height of 13-15 mm and a width of 17-19 mm (e.g., a depth of 13 mm, height of 14 mm and width of 18 mm in one particular embodiment).

At block 128, processing logic receives the intraoral images generated from the intraoral scan. At block 130, processing logic then registers (i.e., "stitches" together) the intraoral images generated from the intraoral scan. This may include registering the first intraoral image to the second intraoral image using at least a portion of the first representation of the adhesive object in the first intraoral image and at least one portion (which may be an equivalent portion of a different portion) of the second representation of the adhesive object in the second intraoral image (block 135). In one embodiment, performing image registration includes capturing 3D data of various points of a surface in multiple images (views from a camera), and registering the images by computing transformations between the images. The images may then be integrated into a common reference frame by applying appropriate transformations to points of each registered image. Image registration is discussed in greater detail with reference to FIG. 2.

At block 140, processing logic then generates a 3D model of the target area based on the registration. The 3D model may be a virtual or digital model showing the surface features of the target area. For a 3D model of a full dental arch, the arch width of the 3D model may be accurate to within 200 microns of the arch width of the patient's actual dental arch.

In one embodiment, after the 3D model of the dental site is generated, representations of the adhesive object (or objects) are subtracted from the 3D model (e.g., via Boolean subtraction). Since the properties (e.g., shape, size, color, surface pattern, etc.) of the adhesive object are known, the representation may be subtracted using these properties. This may leave a gap or empty region on a surface of the 3D model, which may be filled in by interpolating between portions of the dental site surrounding the gap as well as by filling with a surface parallel to the base of the adhesive object. This allows the underlying dental surface to be estimated with reasonable accuracy. Alternatively, a subsequent scan of the underlying dental surface may be added to fill in the missing region by using another registration object placed elsewhere in the arch at a different location, in order to accurately orient and position the intraoral surfaces previously covered up by the registration marker.

Figure 2:
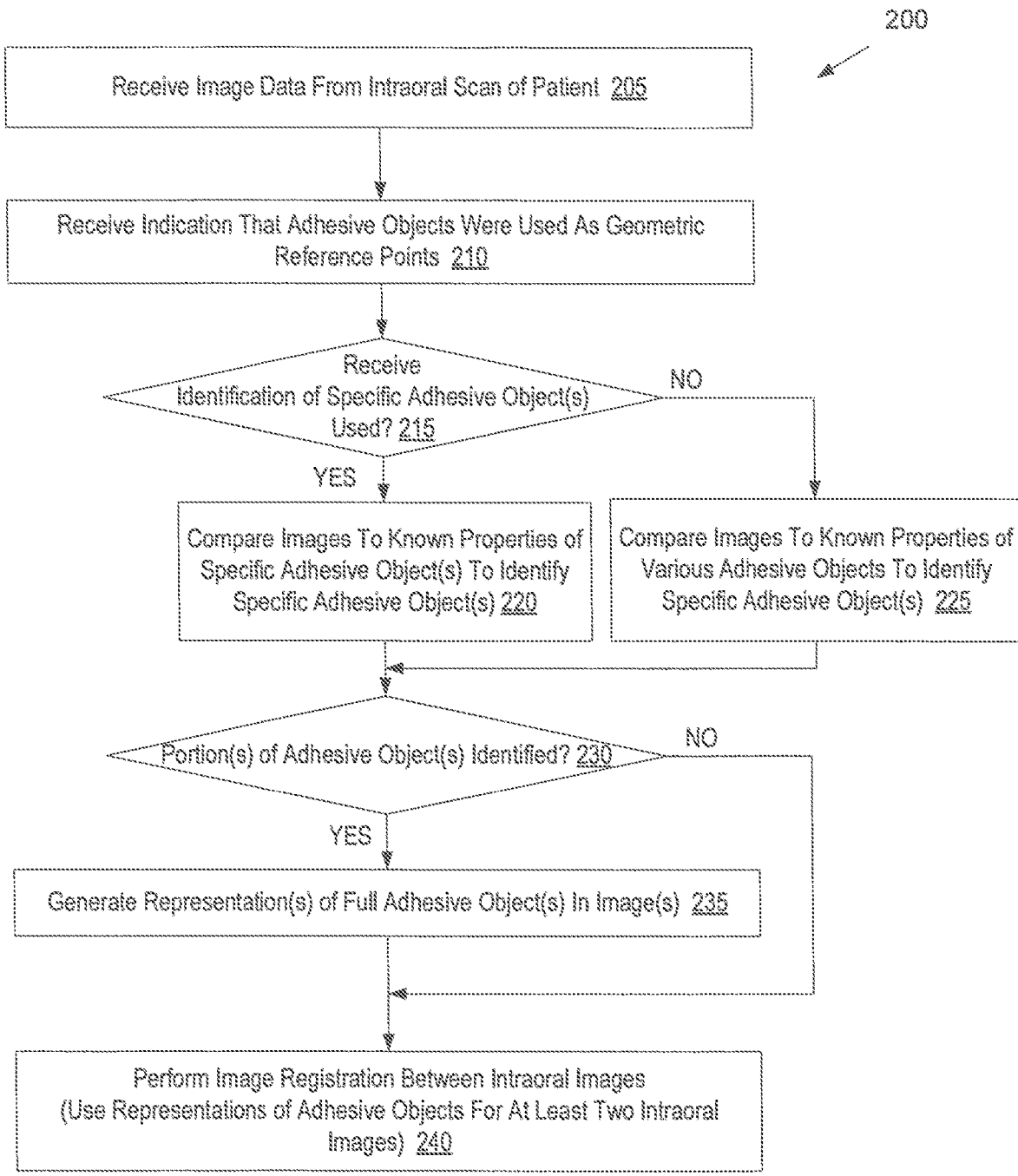
FIG. 2 illustrates a flow diagram for a method of performing image registration of intraoral images, in accordance with embodiments of the present invention.

FIG. 2 illustrates a flow diagram for a method 200 of performing image registration of intraoral images, in accordance with embodiments of the present invention. The method 200 is performed by processing logic that comprises hardware (e.g., circuitry, dedicated logic, programmable logic, microcode, etc.), software (such as instructions run on a processing device), or a combination thereof. In one embodiment, method 200 is performed by a computing device, such as computing device 305 of FIG. 3. In one embodiment, method 200 is performed at block 130 of method 100.

At block 205 of method 200, processing logic receives image data from an intraoral scan of a patient. The image data includes multiple digital intraoral images of a target zone of the dental site. In one embodiment, the multiple digital intraoral images are discrete images. In one embodiment, the multiple digital images are part of a video (e.g., a continuous scan) taken of the dental site. The video may be taken while a dental practitioner moves the intraoral scanner between points within the patients oral cavity. The image data may be received from an intraoral scanner, from a remote computing device, from a local or remote data store, or from another source.

At block 210, processing logic receives an indication that adhesive objects were used as geometric reference points. For example, the dental practitioner may select from a drop down menu that adhesive objects have been affixed to a target area of a dental site. The dental practitioner may further select specific types of adhesive objects that have been used (e.g., identify particular adhesive objects having specific shapes, sizes, colors, patterns, thicknesses, and so forth). Options for different types of adhesive objects may be presented to the dental practitioner in a graphical user interface (e.g., in drop down menus) or via a command line interface. Alternatively, the dental practitioner may manually input the type of adhesive object (e.g., by typing in one or more parameters of the adhesive objects). In one embodiment, each type of adhesive object is associated with a particular identifier (ID), and the dental practitioner may indicate a specific type of adhesive object by selecting or inputting a particular ID.

In one embodiment, at block 215, processing logic determines whether an identification of a specific type of adhesive object (or multiple types of adhesive objects) have been used. If a specific adhesive object or objects are identified, the method may continue to block 220. Otherwise, the method may proceed to block 225. If the operations of block 215 are not performed, then the method may proceed from block 210 to block 225.

At block 220, processing logic compares one or more of the received intraoral images to known properties (parameters) of the specific adhesive object or objects that were specified. The known properties may be stored in a data store that is accessible to processing logic. Based on such a comparison, processing logic may identify representations of the adhesive object in one or more of the intraoral images.

At block 225, processing logic compares received intraoral images to known properties of various adhesive objects to identify specific adhesive objects in one or more intraoral images. The computation performed at block 225 may be greater than the computation performed at block 220 since a greater number of comparisons are performed. Additionally, processing logic may be better able to identify an adhesive object from a distorted image when it is searching for a particular adhesive object that is known to have been used.

Some adhesive objects may have specific colors and/or surface patterns that may be used to detect the adhesive object and/or to determine an orientation of the adhesive object. However, conventional intraoral scanners are configured to detect 3D surfaces, but not to detect colors or two-dimensional (2D) patterns. In contrast, in some embodiments processing logic includes color recognition algorithms, pattern recognition algorithms, and/or object detection algorithms that rely on color and/or texture to enable detection of such adhesive objects. In one embodiment if a dental practitioner has indicated adhesive objects that rely on a 3D shape to be detected, color and pattern recognition algorithms, for example, may be disabled by processing logic. However, if the dental practitioner has indicated an adhesive object that relies on color and/or surface pattern for detection, or if the dental practitioner has failed to indicate any specific adhesive objects, such color recognition, pattern recognition and/or object detection algorithms may be enabled and used to identify adhesive objects. Applying such a color recognition, pattern recognition or object detection algorithm may include analyzing the intraoral images to identify a known color and/or known pattern of an adhesive object. Once the known color or pattern are identified, then a representation of a particular adhesive object having the known color and/or pattern may be identified in an image, and may be recognized as an instance of the adhesive object.

In one embodiment, at block 230 processing logic determines whether portions of adhesive objects have been identified (e.g., whether less than an entirety of an adhesive object has been identified in an intraoral image). If a partial adhesive object is identified, then the method may continue to block 235, at which processing logic may generate a representation of the full adhesive object in the intraoral image. For example, if the image includes one corner of an adhesive object, processing logic may replace the corner with a representation of the full adhesive object. This may improve image registration between images. For example, if two different images contain representations of different non-overlapping portions of an adhesive object, then it may impair an ability of processing logic to determine a proper transformation of the images to align them. However, if the shape of the adhesive object is known, and can be added to the intraoral images, then the images will include overlapping portions of the adhesive object that can be used to compute transformation vectors, and thus facilitate registration of the two intraoral images.

At block 240, processing logic performs image registration between the intraoral images. In particular, processing logic uses representations of the adhesive objects for at least two of the intraoral images to compute transformations that will cause the adhesive objects from the two intraoral images to be aligned. In one embodiment, processing logic performs image registration in a manner discussed in U.S. Pat. No. 6,542,249, issued Apr. 1, 2003, which is incorporated herein by reference.

In one embodiment, image registration is performed for each pair of adjacent or overlapping intraoral images (e.g., each successive frame of an intraoral video). Image registration algorithms are carried out to register two adjacent intraoral images, which essentially involves determination of the transformations which align one image with the other. Each registration between a pair of images may be accurate to within 10-15 microns. Image registration may involve identifying multiple points in each image (e.g., point clouds) of an image pair, surface fitting to the points of each image, and using local searches around points to match points of the two adjacent images. For example, processing logic may match points of one image with the closest points interpolated on the surface of the other image, and iteratively minimize the distance between matched points. Processing logic may also find the best match of curvature features at points of one image with curvature features at points interpolated on the surface of the other image, without iteration. Processing logic may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, processing logic may determine a point match between images, which may take the form of a two dimensional (2D) curvature array. A local search for a matching point feature in a corresponding surface patch of an adjacent image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Processing logic repeats image registration for all adjacent image pairs of a sequence of intraoral images to obtain a transformation between each pair of images, to register each image with the previous one. Processing logic then integrates all images into a single 3D model by applying the appropriate determined transformations to each of the images. Each transformation may include rotations about one to three axes and translations within one to three planes.

Figure 3:
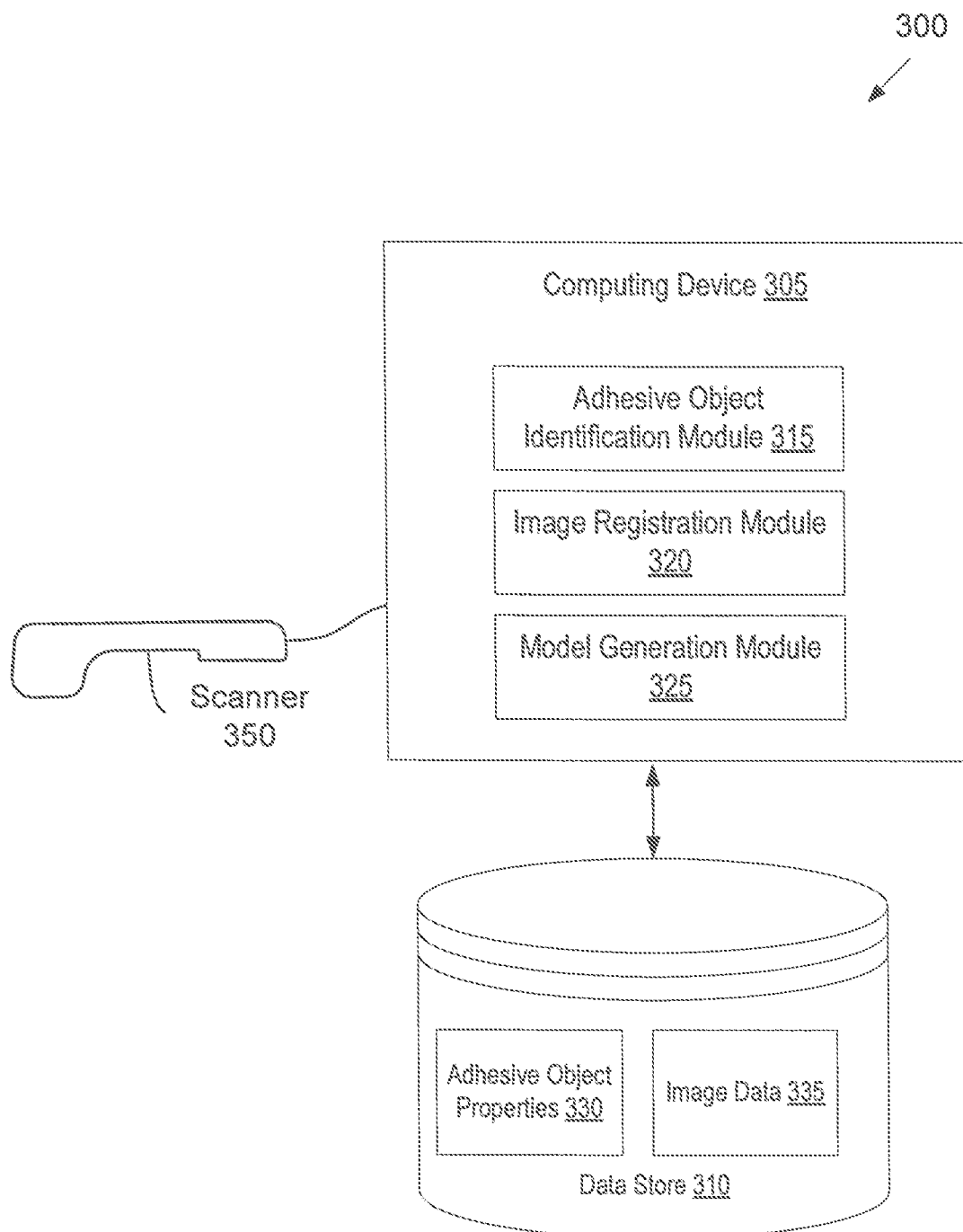
FIG. 3 illustrates one embodiment of a system for performing intraoral scanning and generating a virtual three dimensional model of a dental site.

FIG. 3 illustrates one embodiment of a system 300 for performing intraoral scanning and/or generating a virtual three dimensional model of a dental site. In one embodiment, system 300 carries out one or more operations of above described method 200 and/or method 300. System 300 includes a computing device 305 that may be coupled to a scanner 350 and/or a data store 310.

Computing device 305 may include a processing device, memory, secondary storage, one or more input devices (e.g., such as a keyboard, mouse, tablet, and so on), one or more output devices (e.g., a display, a printer, etc.), and/or other hardware components. Computing device 305 may be connected to a data store 310 either directly or via a network. The network may be a local area network (LAN), a public wide area network (WAN) (e.g., the Internet), a private WAN (e.g., an intranet), or a combination thereof. The computing device and the memory device may be integrated into the scanner in some embodiments to improve performance and mobility.

Data store 310 may be an internal data store, or an external data store that is connected to computing device 305 directly or via a network. Examples of network data stores include a storage area network (SAN), a network attached storage (NAS), and a storage service provided by a cloud computing service provider. Data store 310 may include a file system, a database, or other data storage arrangement.

In some embodiments, a scanner 350 for obtaining three-dimensional (3D) data of a dental site in a patient's oral cavity is also operatively connected to the computing device 305. Scanner 350 may include a probe (e.g., a hand held probe) for optically capturing three dimensional structures (e.g., by confocal focusing of an array of light beams). One example of such a scanner 350 is the iTero® intraoral digital scanner manufactured by Align Technology, Inc. Other examples of intraoral scanners include the 3M™ True Definition Scanner and the Apollo DI intraoral scanner and CEREC AC intraoral scanner manufactured by Sirona®.

The scanner 350 may be used to perform an intraoral scan of a patients oral cavity. A result of the intraoral scan may be a sequence of intraoral images that have been discretely generated (e.g., by pressing on a "generate image" button of the scanner for each image). Alternatively, a result of the intraoral scan may be one or more videos of the patients oral cavity. An operator may start recording the video with the scanner 350 at a first position in the oral cavity, move the scanner 350 within the oral cavity to a second position while the video is being taken, and then stop recording the video. In some embodiments, recording may start automatically as the scanner identifies either teeth or adhesive objects In either case, the scanner 350 may transmit the discrete intraoral images or intraoral video (referred to collectively as image data 335) to the computing device 305. Note that in some embodiments the computing device may be integrated into the scanner 350. Computing device 305 may store the image data 335 in data store 310. Alternatively, scanner 350 may be connected to another system that stores the image data in data store 310. In such an embodiment, scanner 350 may not be connected to computing device 305.

Computing device 305 may include an adhesive object identification module 315, an image registration module 320, and a model generation module 325. Adhesive object identification module 315 may analyze received image data 335 using known adhesive object properties 330 to identify adhesive objects in the intraoral images of the image data 335. The adhesive object properties 330 may be stored in data store 310. In one embodiment, user input identifies specific adhesive objects that have been used, reducing a complexity of the search for adhesive objects. Image registration module 320 registers the intraoral images using the previously described image registration techniques. In one embodiment, image registration module 320 uses an output of the adhesive object identification module 315 when performing the image registration. In other embodiments (e.g., where only 3D adhesive objects with no surface pattern are used), image registration module 320 may perform image registration without using any stored or known information about the adhesive objects. Additionally, in some embodiments adhesive object identification module 315 is not included in computing device 305. After image registration is complete, or as image registration is performed, model generation module 325 generates a 3D virtual model of the imaged dental site.

Figure 4A:
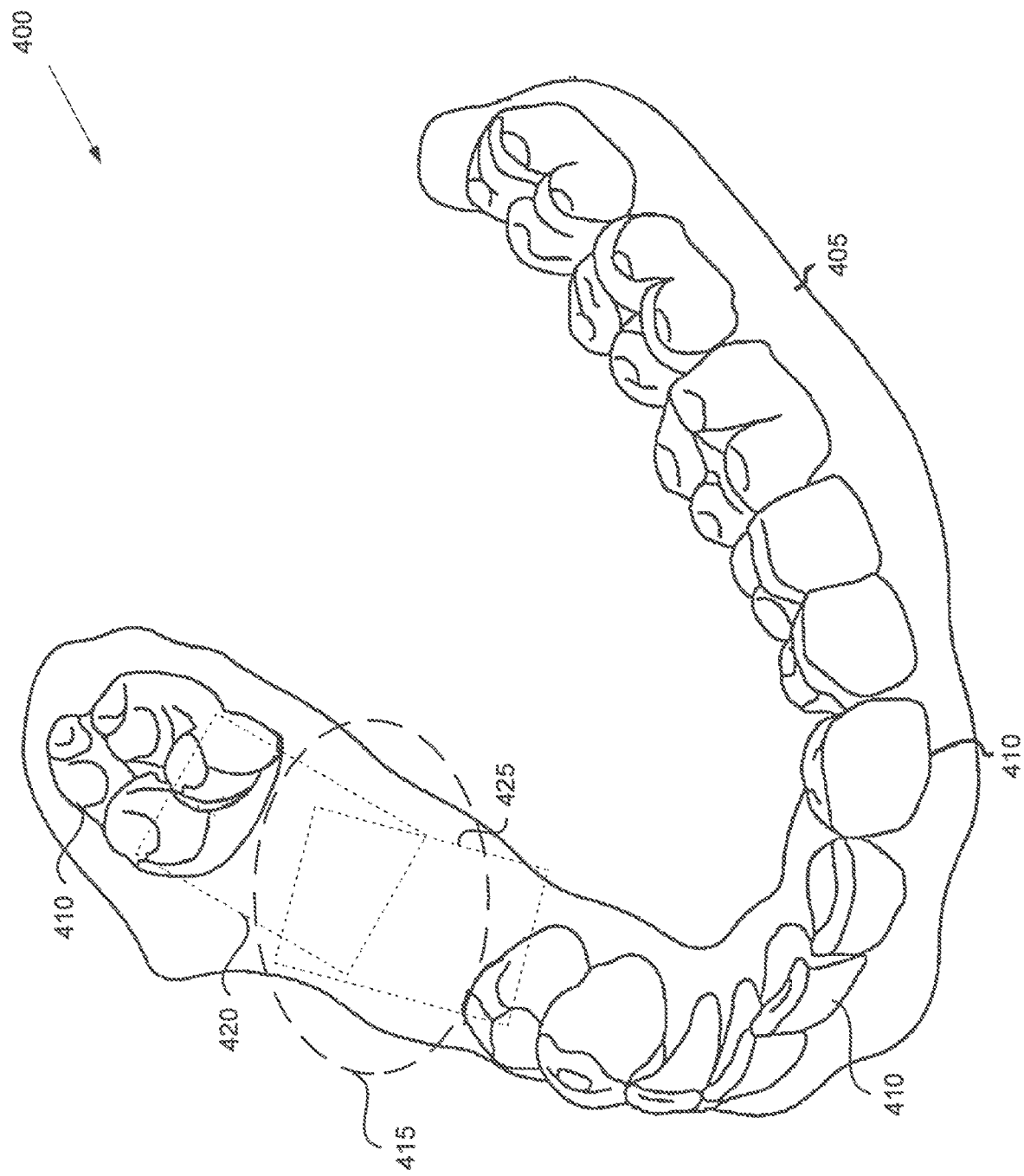
FIG. 4A illustrates a portion of an example dental arch that is missing two teeth.

FIG. 4A illustrates an example dental arch 400 that is missing two teeth. The illustrated dental arch 400 is missing a pair of adjacent teeth at a target zone 415 of the dental arch 400. The dental arch 400 includes gums 405 and multiple teeth 410.

Two intraoral images 420, 425 have been taken of the target zone 415 of the dental arch 400. Each of the intraoral images 420, 425 may have been generated by an intraoral scanner having a particular distance from the dental surface being imaged (e.g., from the dental arch 400). At the particular distance, the intraoral images 420, 425 have a particular scan area and scan depth. The shape and size of the scan area will generally depend on the scanner, and is herein represented by a rectangle. Each image may have its own reference coordinate system and origin. Each intraoral image may be generated by a scanner at a particular position (scanning station). The location and orientation of scanning stations may be selected such that together the intraoral images adequately cover the entire target zone 415. Preferably, scanning stations are selected such that there is overlap between the intraoral images 420, 425 as shown. Typically, the selected scanning stations will differ when different scanners are used for the same target area, depending on the capture characteristics of the scanner used. Thus, a scanner capable of scanning a larger dental area with each scan (e.g., having a larger field of view) will use fewer scanning stations than a scanner that is only capable of capturing 3D data of a relatively smaller dental surface. Similarly, the number and disposition of scanning stations for a scanner having a rectangular scanning grid (and thus providing projected scanning areas in the form of corresponding rectangles) will typically be different from those for a scanner having a circular or triangular scanning grid (which would provide projected scanning areas in the form of corresponding circles or triangles, respectively).

As shown, there are no teeth in the target zone. This lack of teeth makes registration between the two intraoral images 420, 425 challenging because the smooth surfaces when optically captured as partial scans are difficult to accurately stitch together without distinctive registration features within the field of each partial scan.

Figure 4B:
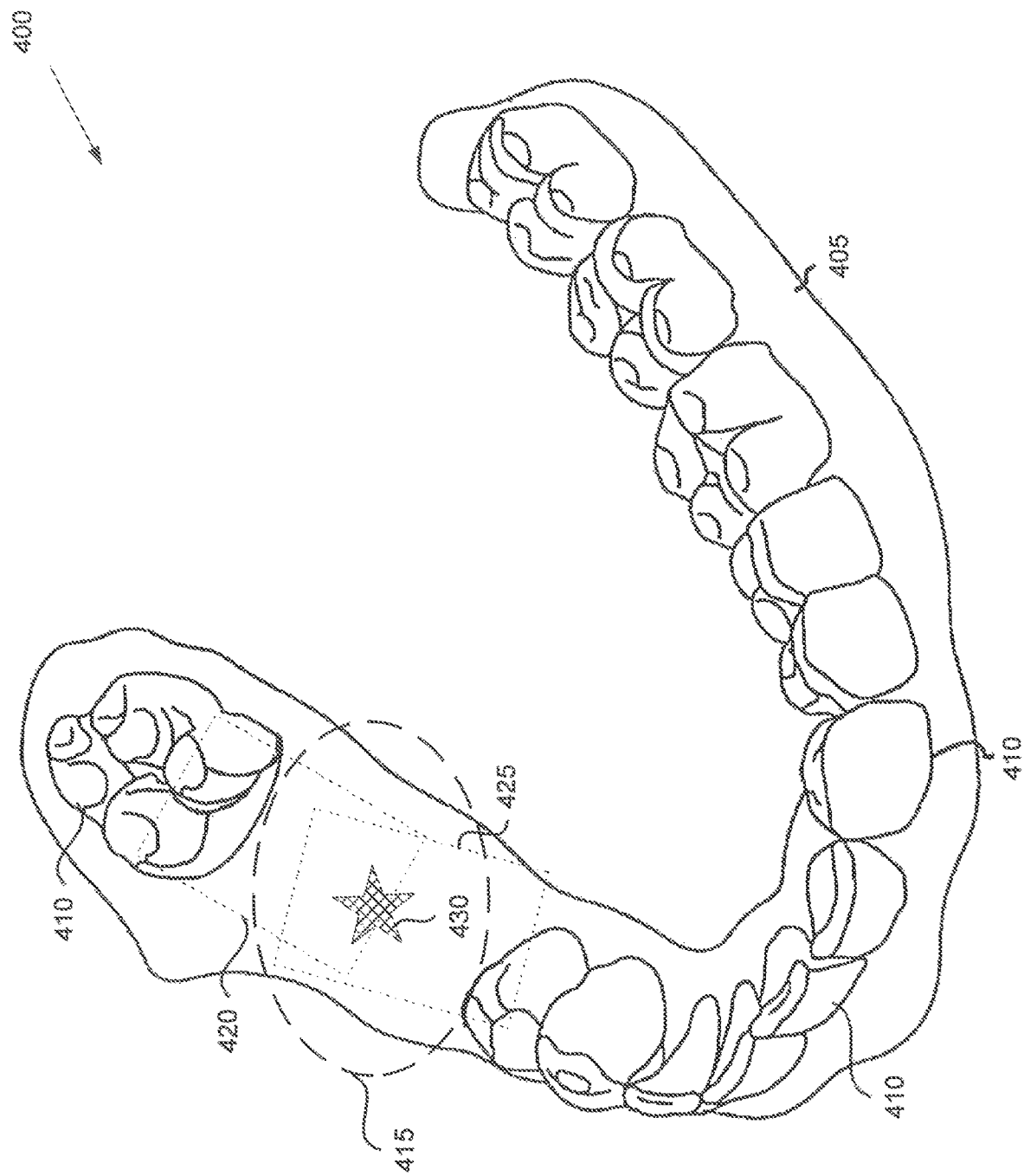
FIG. 4B illustrates the example dental arch of FIG. 4A with the addition of an adhesive object placed at the location of the missing teeth, in accordance with embodiments of the present invention.

FIG. 4B illustrates the oral cavity 400 of FIG. 4A with the addition of an adhesive object 430 placed at the location of the missing teeth, in accordance with embodiments of the present invention. The adhesive object 430 may be placed anywhere on the gum at or near a target area. In one embodiment, the adhesive object is placed at (or approximately at) a gum line near the target area (or where the gum line would be if the target area had teeth). The same intraoral images 420, 425 of the target zone 415 from FIG. 4A are shown, with the exception that the intraoral images include representations of at least a portion of the adhesive object 430.

The adhesive object 430 may be made of a body having a particular shape, an upper surface and a lower surface. The adhesive object may be composed of an edible substance such as a carbohydrate-based substance. Alternatively, the adhesive object may be a pattern of ink that has been stamped or temporarily tattooed onto gingival surfaces at the location of the missing teeth. In one embodiment, the body is composed of a material that does not substantially change its shape (or does not change its shape at all) during intraoral scanning. For example, the body may not degrade or wash away (e.g., by saliva) within the time frame of performing the intraoral scan. In the example of an ink, the ink may retain its pattern during the time frame of the intraoral scan.

In one embodiment, the adhesive object includes a body and an adhesive on a lower surface of the body. In one embodiment, the body is composed of a different substance than the adhesive on the lower surface of the body. In one embodiment, the adhesive is a dry liquid-activated adhesive (e.g., a dry water-activated adhesive). One example of a dry water-activated adhesive that may be used is sodium alginate.

Other adhesives that may be used include cellulose gum, sodium carboxymethyl cellulose, methyl cellulose, polyvinyl methyl ether maleate, gelatin, pectin, karaya, tragacanth, and so on. Any of these adhesives may be used on its own, or as a mixture with other adhesives (e.g., as a mixture with sodium alginate). In one embodiment, the adhesive material includes a thermoplastic ethylene oxide polymer film having a dry water-activated adhesive dissolved and dispersed in the polymer film. For example, any of the aforementioned adhesives may be mixed with an ethylene oxide polymer to form a bonding agent. The water-activated adhesive may include from 0% to approximately 90% by weight of an ethylene oxide polymer/water-activated adhesive mixture, for example. In one embodiment, the adhesive is a film of ethylene oxide sandwiched between superimposed fiber-faced webs. In one particular embodiment, the adhesive includes a combination of mannitol, hydroxypropul cellulose, polyethylene glycol and magnesium stearate. The adhesive may include 60 grams mannitol as a filler, 20 grams hydroxypropyl cellulose as a binder, 18.9 grams polyethylene glycol 800-1000 as a binder, and 1 gram magnesium stearate as a lubricant. In another embodiment, the adhesive includes a combination of mannitol, carbopol, polyethylene glycol and magnesium stearate. The adhesive may include 50 grams mannitol as a filler, 20 grams carbopol 934 as a binder, 28.9 grams polyethulene glycol 800-1000 as a binder, and 1 gram magnesium stearate as a lubricant.

The adhesive object may include a feature on the upper surface of the body that is detectable by an intraoral scanner. Alternatively, in the case of a stamped adhesive object the adhesive object may include a feature stamped directly to a gingival surface. At least one of the shape of the body or the feature on the upper surface provides a geometrical or optical reference point for image registration of images generated by the intraoral scanner.

Figure 7:
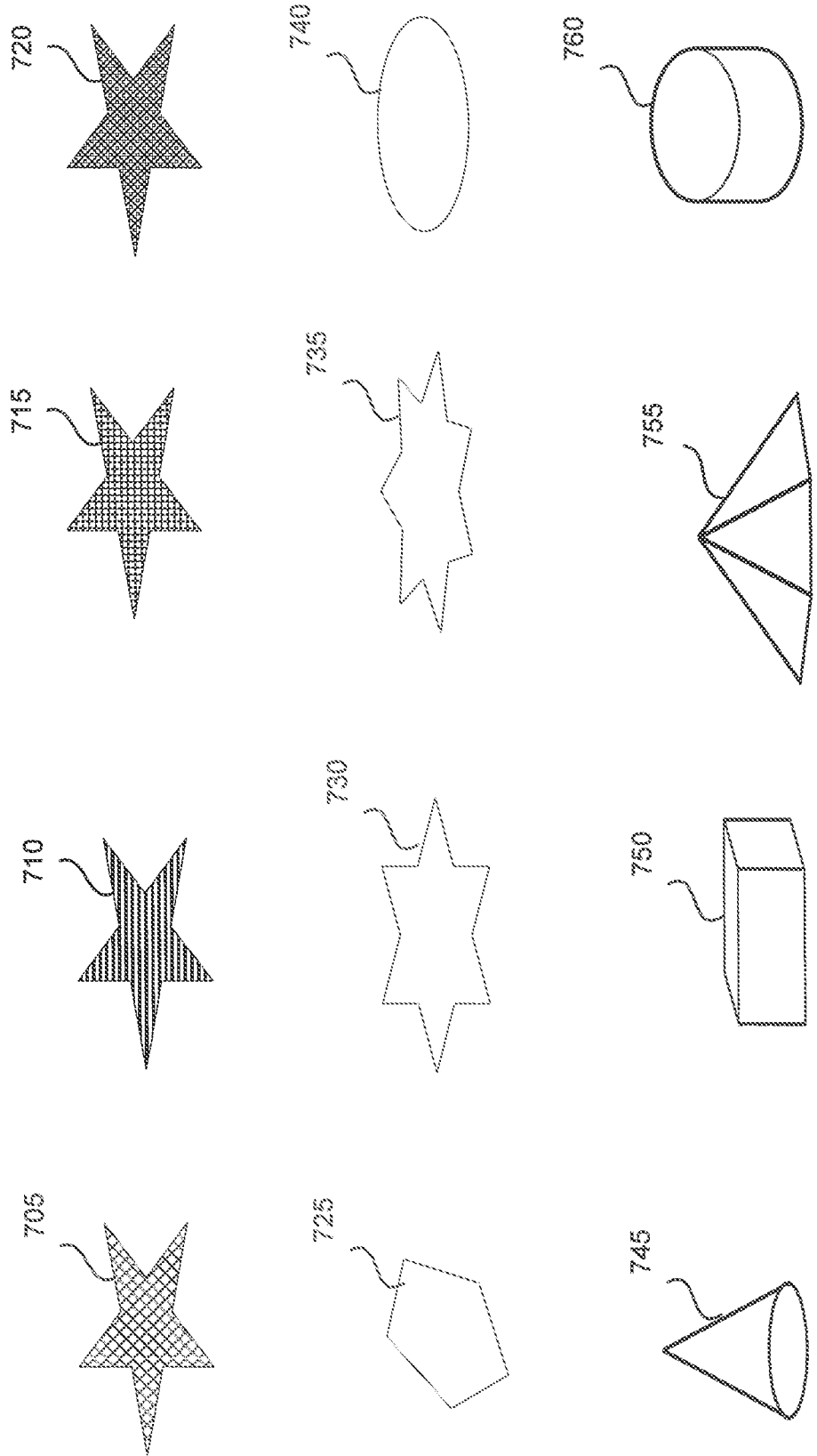
FIG. 7 illustrates example adhesive objects, in accordance with embodiments of the present invention.

FIG. 7 illustrates various examples of adhesive objects. In one embodiment, the feature on the upper surface of the adhesive objects includes a pattern and/or a color (or multiple colors). Examples of patterns that may be used include a checkerboard pattern (e.g., alternating black and white squares), a line pattern, a grid pattern, a 2-D barcode pattern, a random dot pattern, and so on. For example, adhesive object 705 has a star shape and includes a first grid pattern on an upper surface. Adhesive object 710 has a star shape and includes a line pattern on an upper surface. Adhesive object 715 has a star shape and includes a second grid pattern on an upper surface. Adhesive object 720 has a star shape and includes a checkerboard pattern on an upper surface.

Any shape may be used for the adhesive object. For example, adhesive objects 705-720 are five-pointed stars. Adhesive object 725 is a pentagon. Adhesive object 730 is a six-pointed star. Adhesive object 735 is a seven-pointed star. Adhesive object 740 is a circle.

In one embodiment, the adhesive object is substantially flat (e.g., approximately two-dimensional). For example, the adhesive object may have a flat upper surface and a flat lower surface, and may have a thickness of less than 100 microns in one embodiment. Adhesive objects 705-740 may be examples of such flat adhesive objects. In one embodiment, the adhesive object is a pattern of ink stamped onto a gingival surface. The ink may not be susceptible to erosion from the gingival surface within a time frame used to perform an intraoral scan.

In one embodiment, the adhesive object is substantially flat, but has a thickness that is detectable to the intraoral scanner. Thus, the adhesive object may be detected as a three dimensional object. In one embodiment, the adhesive object has a thickness of greater than 20 microns. Adhesive object 760 has a cylindrical shape, and may have a thickness of 20 microns or greater. Adhesive object 750 has a rectangular shape, and may have a thickness of 20 microns or greater. In one embodiment, adhesive object 760 and/or adhesive object 750 have a thickness of 0.5 mm or greater. Note that any of the example adhesive objects 705-740 may also have such thicknesses.

In one embodiment, adhesive object has three dimensional surface features, such as multiple edges, sides, facets, etc. that are detectable to an intraoral scanner. For example, adhesive object 745 has the shape of a cone, and adhesive object 755 has the shape of a pyramid.

Though colors are not shown, any of the example adhesive objects may have solid colors or patterns with various different colors. It should be noted that the illustrated examples of adhesive objects is non-exhaustive, and that any combination of shapes, sizes and/or patterns may be used for adhesive objects. Examples of heights and widths that may be used for adhesive objects are anywhere from 1 mm to 10 mm, though other heights and widths may also be used. It should also be noted that the adhesive objects may be rigid or non-rigid. The shapes of non-rigid adhesive object may change based on the surface that they are affixed to. For example, a stamp on a non-flat gingival surface or a non-rigid sticker on a non-flat gingival surface may be slightly distorted due to a curvature of the gingival surface.

The adhesive objects may be individual adhesive objects as shown in FIG. 7. Such adhesive objects may be distributed in the form of sheets (e.g., sheets of stickers). In one example, the adhesive objects are on a thin long sheet that is approximately wide enough to hold a single adhesive object and long enough to hold many adhesive objects. The sheet may be provided in a roll, which may be inserted into a dispenser. The adhesive objects in the roll may have the same shape, size and/or pattern, or different shapes, sizes and/or patterns. If different shapes, sizes, patterns, etc. are used for the different adhesive objects in the roll, then the sequence may be predetermined and repeatable. For example, the sequence may repeat as a five pointed star, a circle, and a six pointed star, followed by another five pointed star, circle, six pointed star, and so on. In such an embodiment, a computing device that performs image recognition may, after identifying a particular adhesive object, predict adjacent adhesive objects. In one embodiment, the dispenser may have a wheel at one end, which may be rolled along a dental site to deposit adhesive objects at a predetermined spacing.

Figure 8:
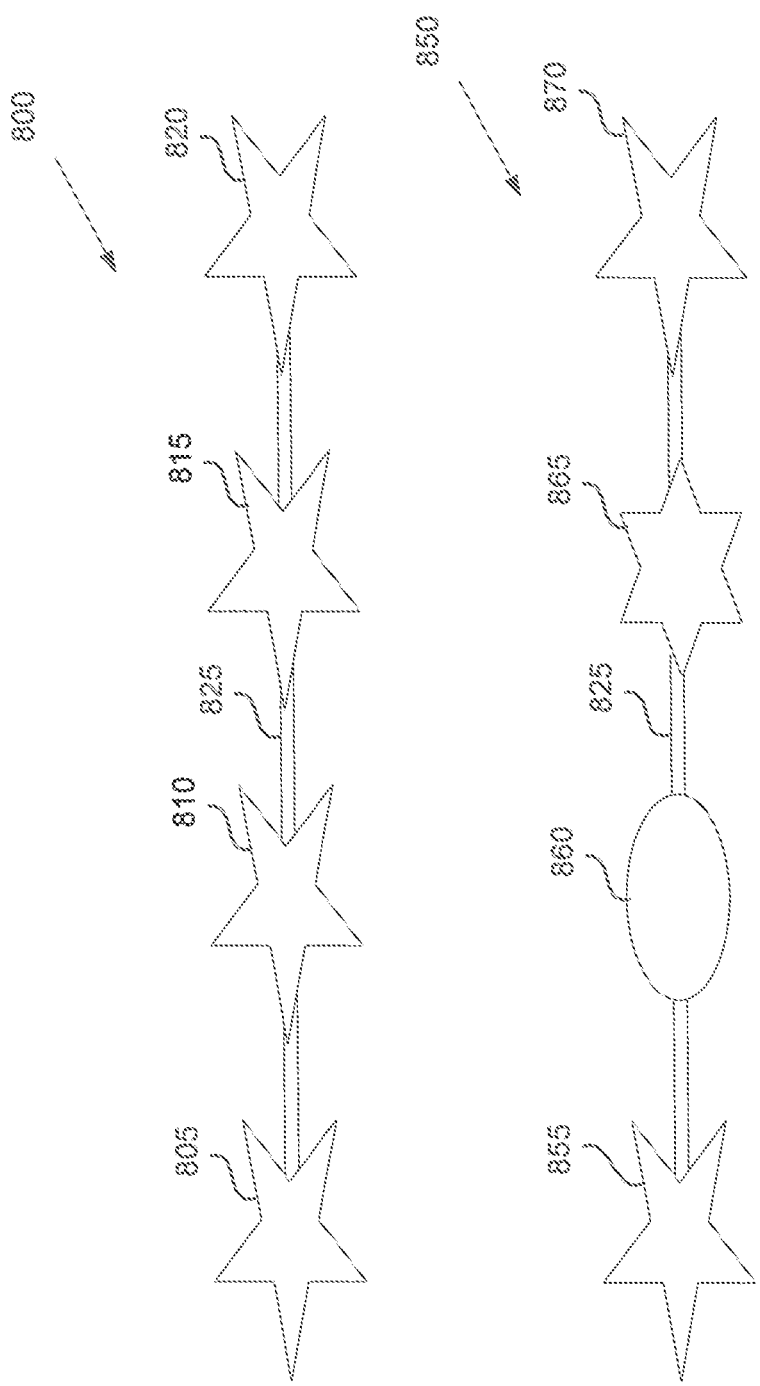
FIG. 8 illustrates example chains of interconnected adhesive objects, in accordance with embodiments of the present invention.

In one embodiment, the adhesive objects are connected together by links, as shown in FIG. 8. Accordingly, an adhesive object may include multiple components that each provide a distinct geometrical reference point, the multiple components being interconnected by a plurality of links. Each component in such a chain may be considered as a separate adhesive object. The links may have a length that ensures that the separation between adjacent adhesive objects will not be greater than the field of view of an intraoral scanner that is to be used. For example, if an intraoral scanner to be used has a field of view with a width of 18 mm, then the links may be shorter than 18 mm. Therefore, intraoral images with adjacent or overlapping fields of view may contain representations of the same adhesive object to enable accurate image registration.

Alternatively, a single long narrow adhesive object may be provided (e.g., such as a tape in a roll) that has many different shapes imprinted on it. The long narrow adhesive object may have a width of 1-10 mm and a length of anywhere from 10-100 mm in some embodiments. Varying patterns and/or colors may also be printed on the long narrow adhesive object in addition to or instead of 3D shapes. The shapes (or colors and/or patterns) may be separated by a regular interval (e.g., every 5 mm, every 10 mm, etc.). Alternatively, the shapes may be separated by varying distances. In one embodiment, only one or a few types of shapes are included in the adhesive object, but there is a varying (e.g., pseudorandom) spacing between the shapes. Alternatively, many (e.g., up to tens to hundreds of) distinct shapes are included in the adhesive object. In one embodiment, each of the shapes is selected so as to have minimal (if any) similar features to the other shapes. For example, a crescent and a cross may be used together because they have no similar features. In one embodiment, the adhesive object is provided as a roll, and a practitioner cuts the roll to create an adhesive object with a custom length that may be sufficient to span an edentulous region. Such an adhesive object may be applied to an edentulous region to span approximately the whole edentulous region.

FIG. 8 shows a first chain 800 of adhesive objects, which includes adhesive objects 805-820, each of which has the same shape, size and pattern. These adhesive objects 805-

820 are interconnected via links 825. Links 825 may be made up of an edible substance (e.g., a sugar based substance). FIG. 8 additionally shows a second chain 850 of adhesive objects, which includes adhesive objects 855-870. The second chain 850 includes an example repeating sequence of different adhesive objects. The sequence includes a five pointed star, a circle, and a six pointed star, which repeats. As shown, adhesive object 855 is a five pointed star, adhesive object 860 is a circle, and adhesive object 865 is a six pointed star, and adhesive object 870 is another five pointed star, staring the sequence over. The first chain 800 and second chain 850 may be distributed in a roll, which may be usable in a dispenser, in one embodiment.

In another embodiment, the adhesive objects are distributed as a stack of adhesive objects (e.g., in a capsule). The adhesive objects in the stack may have the same shape or a different shape. The stack of adhesive objects may be inserted into a dispenser or applicator, which may resemble a pen or syringe in some embodiments. A dental practitioner may place a tip of the applicator onto a dental site and depress a button or plunger, for example, which may cause a single adhesive object to be placed at the dental site. When the applicator empties, it may be refilled with a new stack of adhesive objects. Alternatively, stacks of adhesive objects may be distributed in disposable applicators.

In one embodiment, adhesive objects are initially in a liquid or gel state, and harden into a rigid or semi-rigid adhesive object upon placement at a dental site or upon light or chemical cure. For example, adhesive objects may be composed of a material that swells, hardens, and adheres to a surface when it comes into contact with water. One possible adhesive that adheres responsive to alight or chemical cure is a bis-glycidyl methacrylate (bis-GMA) based resin. A pen or syringe type applicator may have a tip with an opening having a particular shape (e.g., a star shaped opening). A dental practitioner may place a tip of the applicator against a dental site and depress a button or plunger, which may cause an amount of liquid or gel to be extruded through the opening onto the dental site. The gel or liquid may form an adhesive object having the shape of the opening at the applicator's tip, and may harden and adhere on contact with the dental site or upon activation by light or chemical cure. The size of the extruded adhesive object may be dependent on a size of the opening and on an amount of gel or liquid that is extruded.

Referring back to FIG. 4B, an adhesive object 430 has been placed in a particular target zone 415 of a dental arch 400 to facilitate image registration. The adhesive object 430 may be any of the aforementioned adhesive objects. A first intraoral image 420 and a second intraoral image 425 are taken of the target area 415, and each include a representation of the adhesive object 430.

Figure 5A:
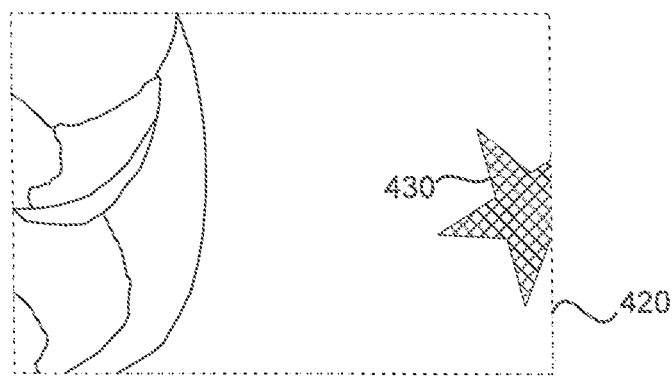
FIG. 5A illustrates a first intraoral image that includes a first representation of an adhesive object, in accordance with one embodiment of the present invention.
Figure 5B:
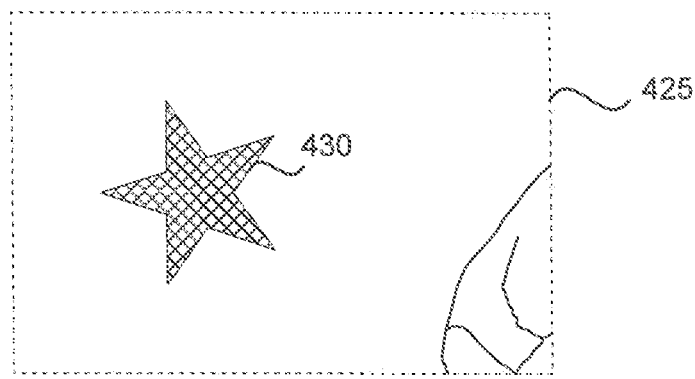
FIG. 5B illustrates a second intraoral image that includes a second representation of an adhesive object, in accordance with one embodiment of the present invention.

FIG. 5A, illustrates first intraoral image 420, which includes a first representation of adhesive object 430, in accordance with one embodiment of the present invention. FIG. 5B illustrates second intraoral image 425, which includes a second representation of adhesive object 430, in accordance with one embodiment of the present invention. As shown, the first representation of adhesive object 430 in the first intraoral image 420 is of only a portion of the adhesive object 430. This partial representation is sufficient for image registration.

Figure 5C:
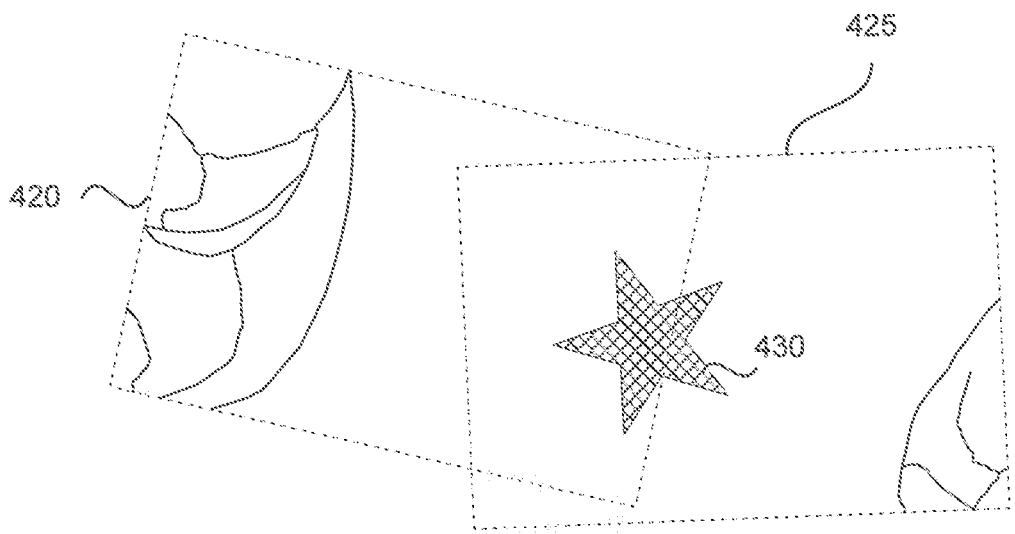
FIG. 5C illustrates a successful image registration of the first intraoral image of FIG. 5A and the second intraoral image of FIG. 5B, in accordance with one embodiment of the present invention.

FIG. 5C illustrates a successful image registration of the first intraoral image 420 of FIG. 5A and the second intraoral image 425 of FIG. 5B, in accordance with one embodiment of the present invention. As shown, transformations have been performed in one or both of the first intraoral image 420 and second intraoral image 425 to cause the first representation of the adhesive object 430 to line up with the second representation of the adhesive object 430. Such transformations may include rotations around up to three axes and translations in up to three planes.

Figure 5D:
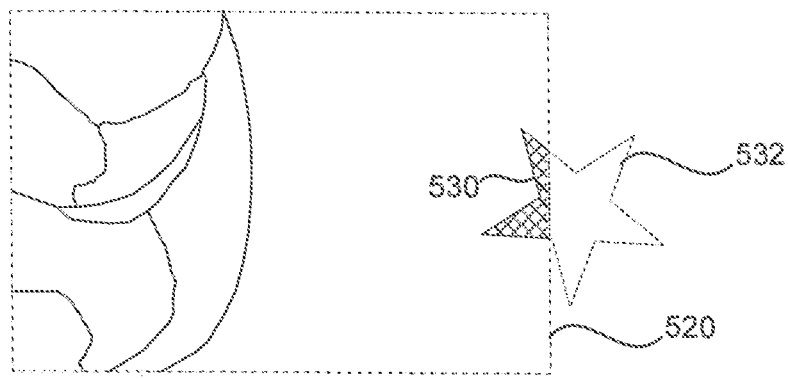
FIG. 5D illustrates a first intraoral image that includes a first representation of a portion of an adhesive object, in accordance with one embodiment of the present invention.
Figure 5E:
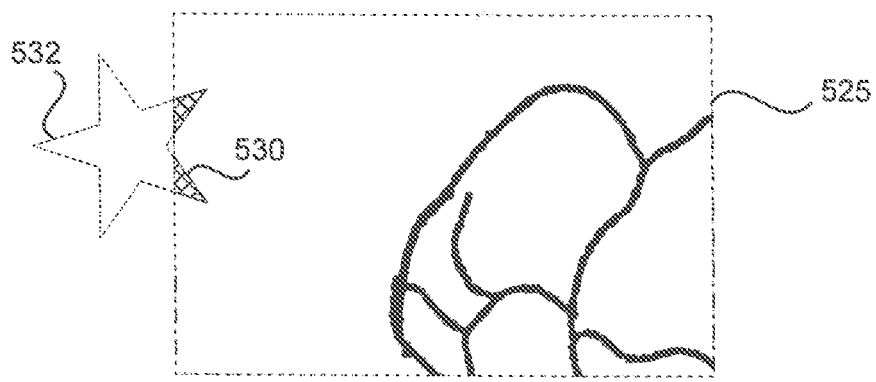
FIG. 5E illustrates a second intraoral image that includes a second representation of a different portion of the adhesive object, in accordance with one embodiment of the present invention.
Figure 5F:
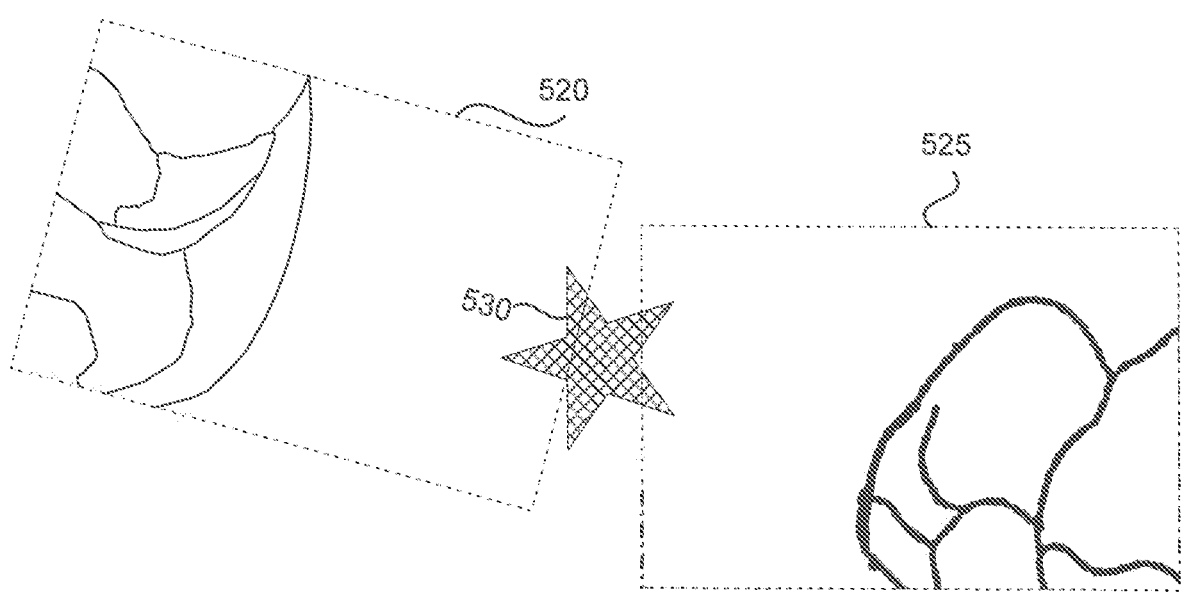
FIG. 5F illustrates a successful image registration of the first intraoral image of FIG. 5D and the second intraoral image of FIG. 5E, in accordance with one embodiment of the present invention.

FIG. 5D illustrates a first intraoral image 520, which includes a first representation of a first portion of an adhesive object 530, in accordance with one embodiment of the present invention. FIG. 5E illustrates a second intraoral image 525, which includes a second representation of a second portion of the adhesive object 530, in accordance with one embodiment of the present invention. As shown, the first representation of adhesive object 530 and the second representation of the adhesive object 530 each include a different portion of the adhesive object. This may cause image registration between these two images to be difficult. However, in some embodiments the system that performs the image registration includes information identifying the shape, size, pattern, and/or other information of the adhesive object. This enables the system to extrapolate the shape and orientation of the rest of the adhesive object to form a virtual representation of the adhesive object 532 from each of the representations of the adhesive object 530. The virtual representation 532 can be used to successfully stitch the two intraoral images together, as shown in FIG. 5F, even though there may be no or minimal overlap between the intraoral images 520, 525.

Figure 5G:
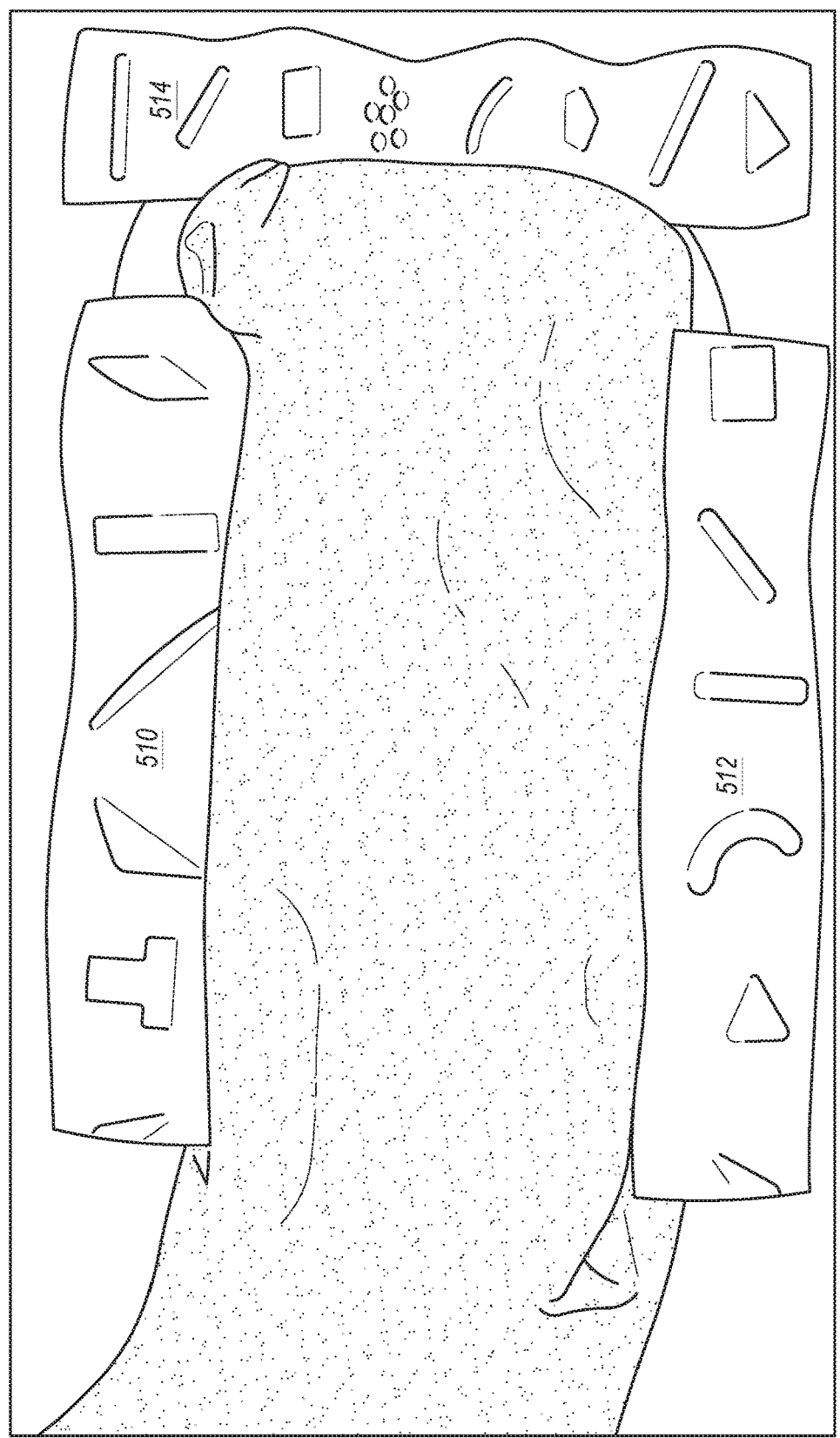
FIG. 5G illustrates a typodont, in accordance with one embodiment.

FIG. 5G illustrates a typodont 505, in accordance with one embodiment. The typodont 505 includes adhesive objects 510-514 disposed around the typodont 505. Alternatively, the adhesive objects may be affixed directly to the typodont. The adhesive object may be a one or more long thin bodies with multiple patterns or shapes imprinted thereon as shown. Alternatively, multiple distinct adhesive objects of varying shapes and/or sizes may be used. For example, as shown different shapes may include a T shape, a triangle shape, a C shape, a vertical bar shape, a diagonal bar shape, a diamond shape, a square shape, and so on. In one embodiment, adjacent adhesive objects have different shapes.

Figure 5H:
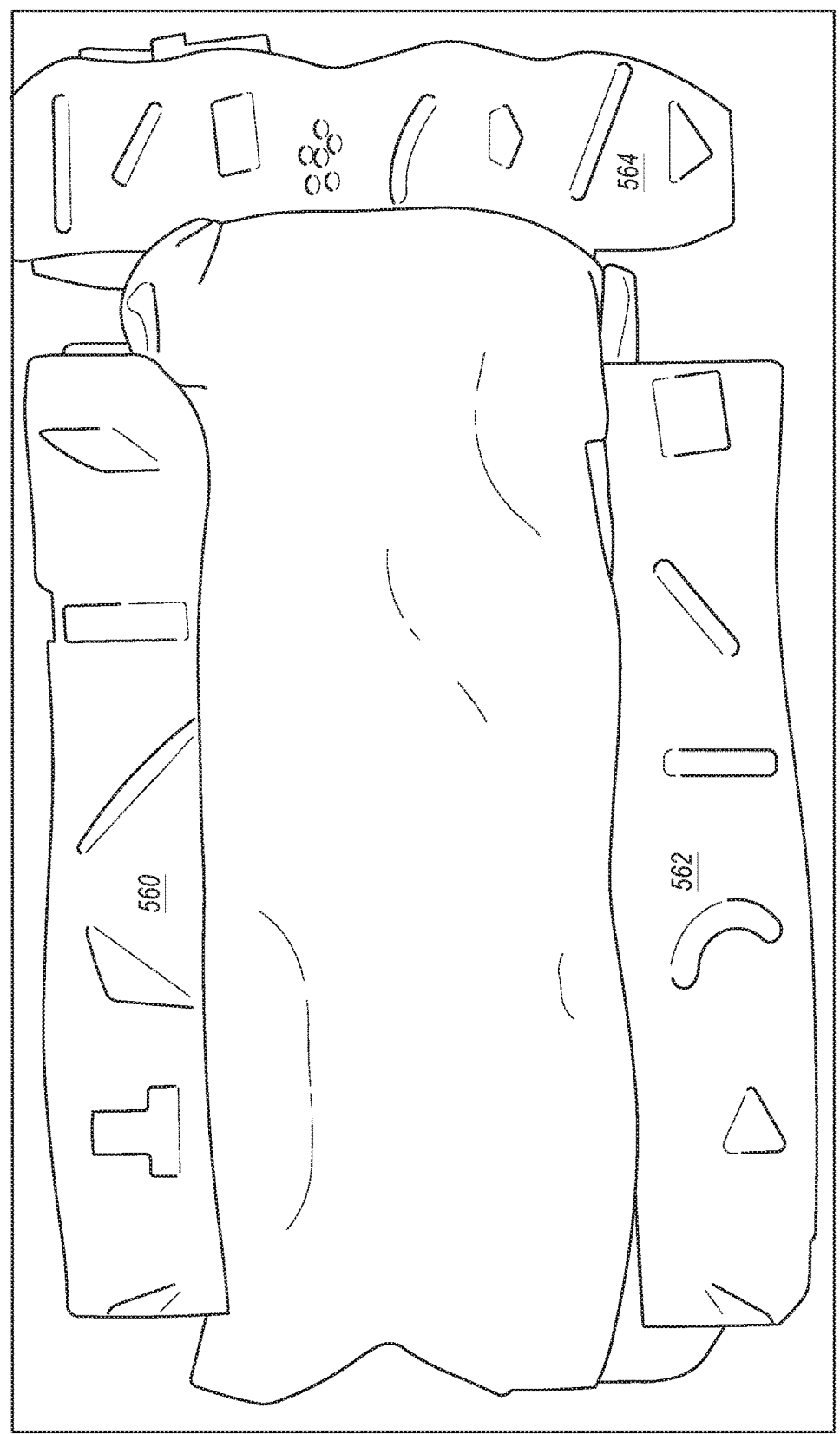
FIG. 5H illustrates a reconstruction of a typodont, in accordance with one embodiment.

FIG. 5H illustrates a reconstruction 555 of the typodont 505. An intraoral scan including multiple discrete images or a video of the typodont 505 has been taken. The images were stitched together and used to construct a virtual model including the reconstructed typodont 555 and reconstructed adhesive objects 560-564. In one embodiment, as shown, the adhesive objects have multiple different shapes. Use of adhesive object with varying shapes may improve an accuracy of image registration. An intraoral scan performed without the adhesive objects would be unsuccessful because there are insufficient surface features to stitch images together. Similar results are achieved for scans of edentulous regions of an oral cavity.

Figure 6A:
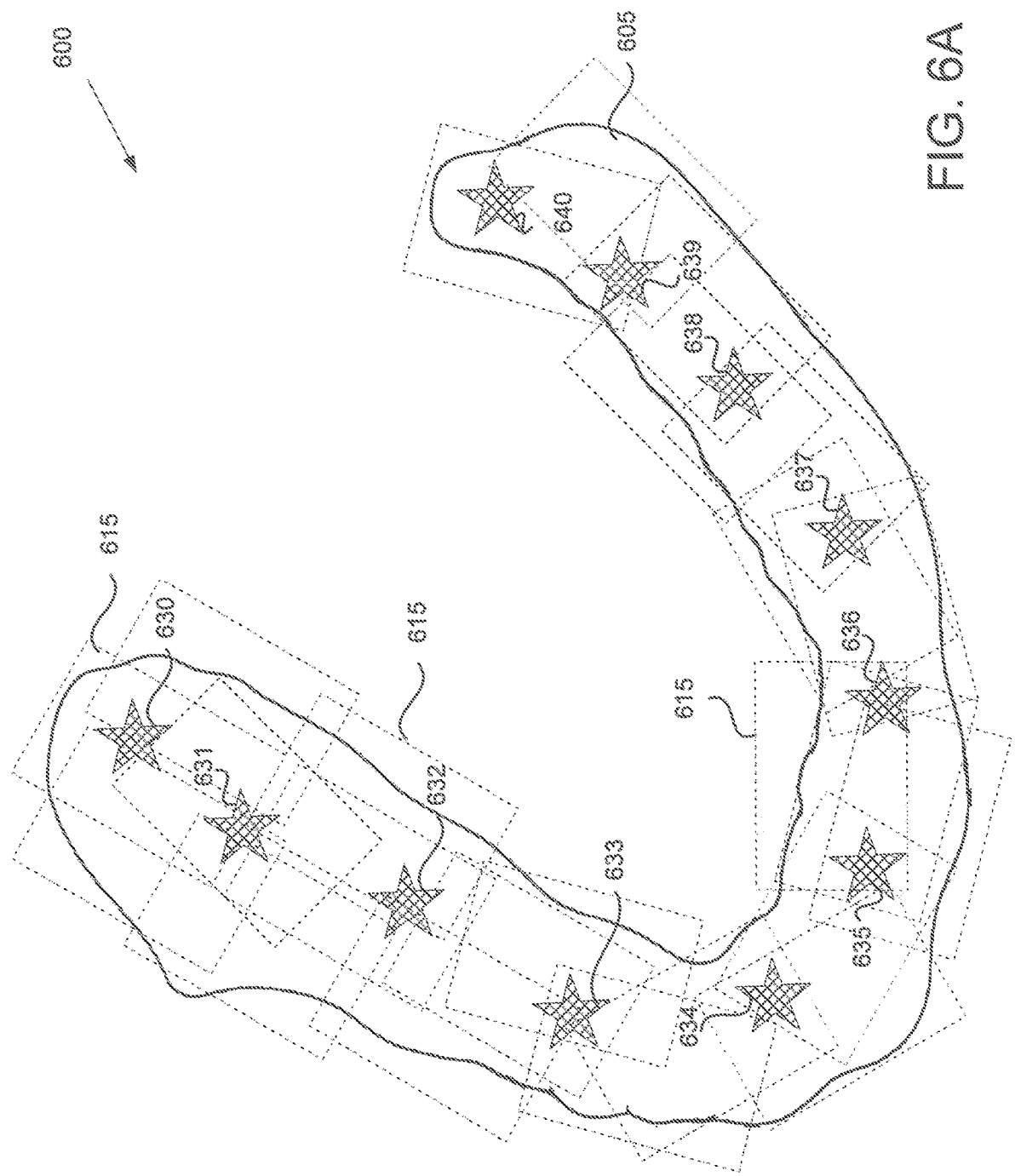
FIG. 6A illustrates a portion of an edentulous arch with the addition of a pattern of adhesive objects placed at various locations, in accordance with embodiments of the present invention.

FIG. 6A illustrates an edentulous arch 600 with the addition of a pattern of adhesive objects 630-640 placed at various locations, in accordance with embodiments of the present invention. The placement of the adhesive objects at various locations along the edentulous arch 600 enables the edentulous arch 600 to be accurately modeled using intraoral scanning techniques. The placement pattern of the adhesive objects may be determined by a dental practitioner, or may be determined by a computing device based on a field of view of a scanner to be used. A sequence of intraoral images 615 may be taken, which when taken together may depict the entire edentulous arch 600. These intraoral images may be registered with one another using representations of the adhesive objects 630-640 to generate a 3D virtual model or simulation of the edentulous arch 600. This 3D virtual model may be used to manufacture dentures and/or implant abutments. In one example, the generated 3D virtual model of the edentulous arch 600 may be used to develop a treatment plan for an all-on-4® dental implant-supported denture. The all-on-4 dental implant uses four implants abutments (with underlying implants) to support a fixed prosthesis representing 12 to 14 teeth.

Figure 6B:
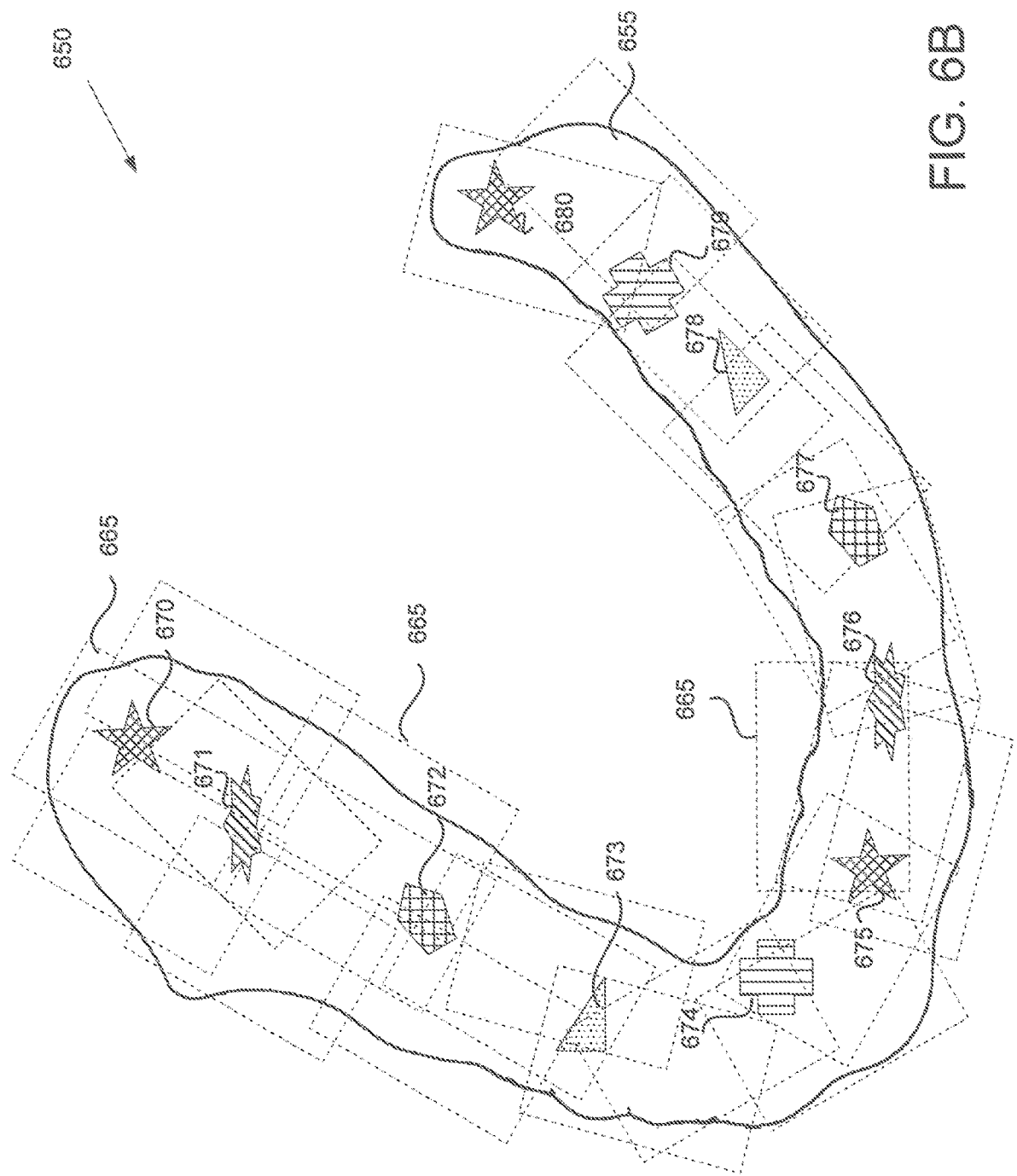
FIG. 6B illustrates a portion of an edentulous arch with the addition of a pattern of adhesive objects placed at various locations, in accordance with embodiments of the present invention.

FIG. 8B illustrates an edentulous arch 650 with the addition of a pattern of adhesive objects 670-680 placed at various locations, in accordance with embodiments of the present invention. The placement of the adhesive objects at various locations along the edentulous arch 650 enables the edentulous arch 650 to be accurately modeled using intraoral scanning techniques. A sequence of intraoral images 665 may be taken, which when taken together may depict the entire edentulous arch 650. These intraoral images may be registered with one another using representations of the adhesive objects 670-680 to generate a 3D virtual model or simulation of the edentulous arch 650. As shown in FIG. 6B, multiple different shapes, sizes and/or patterns of adhesive objects may be used together. For example, a first adhesive object 670 may be a five pointed star, a second adhesive object 671 may be a six pointed star, a third adhesive object 672 may be a pentagon, a fourth adhesive object 672 may be a triangle, a fifth adhesive object 674 may be a cross, and so on. Use of multiple different shapes may improve an accuracy of image registration in some embodiments.

Adhesive objects may be applied by an intraoral applicator. In one embodiment, the intraoral applicator applies temporary tattoo or ink based adhesive objects. The intraoral applicator may be a pen type applicator having a tip with a particular shape that has been carved, molded, laser engraved or vulcanized into the tip. The tip may be a rubber tip that is pressed into an ink well to collect ink and then pressed against a gingival surface to transfer the ink to the gingival surface. The transferred ink will have the particular shape of the tip. In another embodiment, the intraoral applicator applies other types of adhesive objects such as stickers onto a gingival surface.

Figure 9:
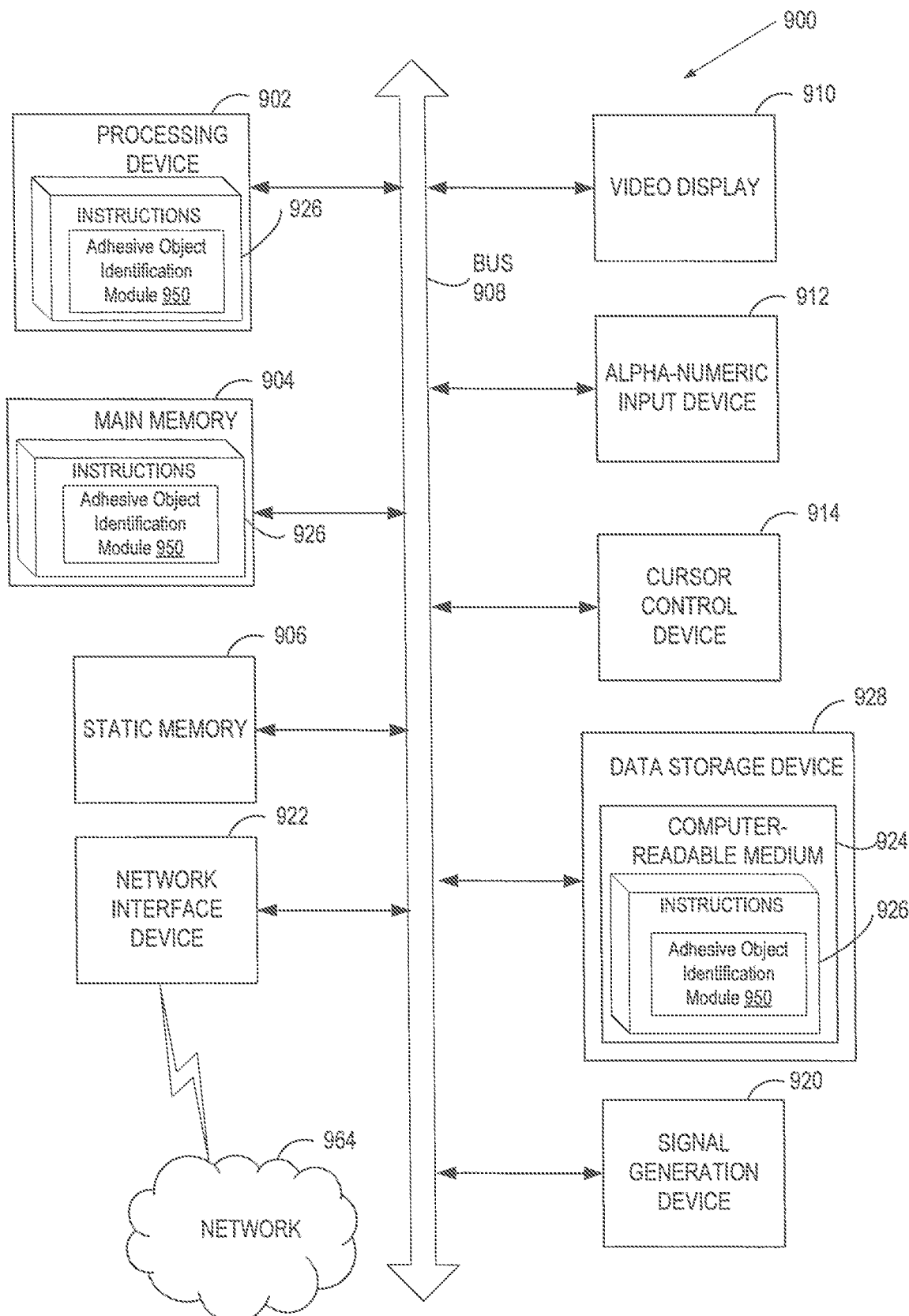
FIG. 9 illustrates a block diagram of an example computing device, in accordance with embodiments of the present invention.

FIG. 9 illustrates a diagrammatic representation of a machine in the example form of a computing device 900 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also betaken to include any collection of machines (e.g., computers) that individually or jointly execute a set (or multiple sets) of instructions to perform any one or more of the methodologies discussed herein.

The example computing device 900 includes a processing device 902, a main memory 904 (e.g., read-only memory (ROM), flash memory, dynamic random access memory (DRAM) such as synchronous DRAM (SDRAM), etc.), a static memory 906 (e.g., flash memory, static random access memory (SRAM), etc.), and a secondary memory (e.g., a data storage device 928), which communicate with each other via a bus 908.

Processing device 902 represents one or more general-purpose processors such as a microprocessor, central processing unit, or the like. More particularly, the processing device 902 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 902 may also be one or more special-purpose processing devices such as an application specific integrated circuit (ASIC), a field programmable gate array (FPGA), a digital signal processor (DSP), network processor, or the like. Processing device 902 is configured to execute the processing logic (instructions 926) for performing operations and steps discussed herein.

The computing device 900 may further include a network interface device 922 for communicating with a network 964. The computing device 900 also may include a video display unit 910 (e.g., a liquid crystal display (LCD) or a cathode ray tube (CRT)), an alphanumeric input device 912 (e.g., a keyboard), a cursor control device 914 (e.g., a mouse), and a signal generation device 920 (e.g., a speaker).

The data storage device 928 may include a machine-readable storage medium (or more specifically a non-transitory computer-readable storage medium) 924 on which is stored one or more sets of instructions 926 embodying any one or more of the methodologies or functions described herein. Wherein a non-transitory storage medium refers to a storage medium other than a carrier wave. The instructions 926 may also reside, completely or at least partially, within the main memory 904 and/or within the processing device 902 during execution thereof by the computer device 900, the main memory 904 and the processing device 902 also constituting computer-readable storage media.

The computer-readable storage medium 924 may also be used to store an adhesive object identification module 950, an image registration module and/or a model generation module, which may correspond to similarly named components of FIG. 3. The computer readable storage medium 924 may also store a software library containing methods that call an adhesive object identification module 950, an image registration module and/or a model generation module. While the computer-readable storage medium 924 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A computer readable medium comprising instructions that, when executed by a processing device, cause the processing device to perform operations comprising:
receiving, by the processing device, intraoral scan data comprising a plurality of intraoral images of a dental site generated during scanning of the dental site by an intraoral scanner, a plurality of ink markings each comprising a pattern of ink having been temporarily stamped or tattooed onto a gingival surface at the dental site prior to the scanning of the dental site, wherein at least two intraoral images of the plurality of intraoral images comprise representations of one or more ink markings of the plurality of ink markings;
performing, by the processing device, registration between the plurality of intraoral images based at least in part on the one or more ink markings;
generating a three-dimensional (3D) model of the dental site using the plurality of intraoral images that have undergone registration; and
outputting the generated 3D model to a display.

2. The computer readable medium of claim 1, the operations further comprising:
using the representations of the one or more ink markings in the at least two intraoral images in performing the registration.

3. The computer readable medium of claim 2, wherein the one or more ink markings provide at least one of an optical or geometrical reference point for performing the registration between the at least two intraoral images, the operations further comprising:
aligning a first representation of at least a first portion of the one or more ink markings in a first intraoral image of the at least two intraoral images with a second representation of at least a second portion of the one or more ink markings in a second intraoral image of the at least two intraoral images to perform the registration.

4. The computer readable medium of claim 1, wherein the one or more ink markings comprise a stamp having a known two-dimensional (2D) shape.

5. The computer readable medium of claim 4, wherein the stamp partially deforms based on a shape of an area on which the stamp was applied, and wherein partial deformation of the stamp deforms the known 2D shape.

6. The computer readable medium of claim 1, the operations further comprising:
outputting a representation of the one or more of the plurality of ink markings on the 3D model of the dental site.

7. The computer readable medium of claim 1, wherein plurality of ink markings are spread apart over an edentulous region of the dental site.

8. The computer readable medium of claim 1, wherein the one or more ink markings have a known color, and wherein the known color is usable to identify the one or more ink markings in the at least two intraoral images.

9. The computer readable medium of claim 1, the operations further comprising: identifying a spatial relationship between a plurality of features of the dental site; determining that a region of the dental site comprises one or more missing teeth; determining that the region of the dental site lacks features suitable for scanning of the dental site; computing an optimal location within the region for placement of the one or more ink markings based on the one or more missing teeth and a field of view of the intraoral scanner; and
indicating the optimal location within the region for placement of the one or more ink markings.

10. The computer readable medium of claim 1, the operations further comprising: presenting a plurality of different ink markings to select from; and
receiving a selection of an ink marking from the plurality of different ink markings, wherein the selected ink marking corresponds to the plurality of ink markings in the intraoral scan data.

11. A system comprising:
an intraoral scanner configured to generate intraoral scan data comprising a plurality of intraoral images of a dental site, each intraoral image of the plurality of intraoral images comprising optically-captured three-dimensional structures of the dental site; and
a computing device operatively coupled to the intraoral scanner, the computing device to:
receive the intraoral scan data comprising the plurality of intraoral images of the dental site generated during scanning of the dental site by the intraoral scanner, a plurality of ink markings each comprising a pattern of ink having been directly applied onto a gingival surface at the dental site prior to the scanning of the dental site, wherein at least two intraoral images of the plurality of intraoral images comprise representations of one or more ink markings of the plurality of ink markings;
perform registration between the plurality of intraoral images based at least on part on the one or more ink markings;
generate a three-dimensional (3D) model of the dental site using the plurality of intraoral images that have undergone registration; and
output the 3D model to a display.

12. The system of claim 11, wherein the 3D model of the dental site comprises a representation of the one or more ink markings that were directly applied onto the gingival surface at the dental site prior to the scanning of the dental site.

13. The system of claim 11, wherein the one or more ink markings comprise a first ink marking having at least one of a first shape, symbol or color and a second ink marking having at least one of a second shape, symbol or color that is different from the at least one of the first shape, symbol or color.

14. The system of claim 11, wherein the one or more ink markings provide at least one of an optical or geometrical reference point for performing the registration between the at least two intraoral images, and wherein the computing device is to align a first representation of at least a first portion of the one or more ink markings in a first intraoral image of the at least two intraoral images with a second representation of at least a second portion of the one or more ink markings in a second intraoral image of the at least two intraoral images to perform the registration.

15. The system of claim 11, wherein the one or ink markings have a known two-dimensional (2D) shape.

16. The system of claim 15, wherein the one or more ink markings partially deform based on a shape of an area on which the one or more ink markings were applied, and wherein partial deformation of the one or more ink markings partially deforms the known 2D shape.

17. The system of claim 11, wherein the one or more ink markings are disposed at an edentulous region of the dental site.

18. The system of claim 11, wherein the one or more ink markings have a known color, and wherein the known color is usable to identify the one or more ink markings in the at least two intraoral images.

19. The system of claim 11, wherein the computing device is further to:
- identify a spatial relationship between a plurality of features of the dental site; determine that a region of the dental site comprises one or more missing teeth;
- determine that the region of the dental site lacks features suitable for scanning of the dental site; compute an optimal location within the region for placement of the one or more ink markings based
- on the one or more missing teeth and a field of view of the intraoral scanner; and
- indicate the optimal location within the region for placement of the one or more ink markings.

20. The system of claim 11, wherein the plurality of ink markings are spaced apart over a region of interest on the dental site.

\* \* \* \* \*